(12) United States Patent
Kitamura et al.

(10) Patent No.: US 7,781,485 B2
(45) Date of Patent: Aug. 24, 2010

(54) HSP90 FAMILY PROTEIN INHIBITORS

(75) Inventors: Yushi Kitamura, Sakai (JP); Yutaka Kanda, Tokyo (JP); Takayuki Nakashima, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 656 days.

(21) Appl. No.: 11/718,079

(22) PCT Filed: Nov. 9, 2005

(86) PCT No.: PCT/JP2005/020519
§ 371 (c)(1),
(2), (4) Date: Apr. 26, 2007

(87) PCT Pub. No.: WO2006/051808
PCT Pub. Date: May 18, 2006

(65) Prior Publication Data
US 2007/0265268 A1    Nov. 15, 2007

(30) Foreign Application Priority Data
Nov. 9, 2004   (JP) .............................. 2004-324480

(51) Int. Cl.
*A61K 31/24*   (2006.01)
*A61K 31/235*   (2006.01)

(52) U.S. Cl. ............... 514/538; 514/237.5; 514/255.01; 514/330; 514/357; 514/423; 514/533; 514/544; 514/620

(58) Field of Classification Search ............... 514/237.5, 514/255.01, 330, 357, 423, 533, 538, 544, 514/620; 544/170, 171, 174, 391; 546/225, 546/336; 548/572; 560/42, 65, 67; 564/165
See application file for complete search history.

(56) References Cited

U.S. PATENT DOCUMENTS 7,538,224 B2 *  5/2009  Nara et al. ................... 546/234
7,538,241 B2 *  5/2009  Kitamura et al. ............ 558/414

FOREIGN PATENT DOCUMENTS

| JP | 3-271222 | 12/1991 |
|----|----------|---------|
| JP | 3-271261 | 12/1991 |
| WO | WO 01/07429 | 2/2001 |
| WO | WO 01/44172 | 6/2001 |
| WO | WO 03/103655 | 12/2003 |
| WO | WO 2004/072051 | 8/2004 |
| WO | WO 2005/000778 | 1/2005 |
| WO | WO 2005/007151 | 1/2005 |
| WO | WO 2005/063222 | 7/2005 |

OTHER PUBLICATIONS

Soman et al, J. Nat. Prod., 1999, 62, 386,388.*
Carter at al, Chemotherapy of cancer, John Wiley & Sons, Second Edition, pp. 361-365, 1981.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, 451 & 596.*
Wolff, M.E. "Burqer's Medicinal Chemistry 4th Ed. Part I", Wiley: New York, 1979, 336-337.*
West, Anthony R., Solid State Chemistry and its Applications, Wiley, New York, 1988, pp. 358 & 365.*
Takasaki, et al., "Inhibitors of Skin-Tumor Promotion. XIII. Inhibitory Effects of Euglobals and . . . ", Biol. Pharm. Bull., vol. 18, No. 2 (1995), 288-94.
Honda, et al., "Inhibitory effects of 3-nitrophloroglucinecarboxylic acid derivatives on . . . ", Cancer Letters, vol. 68, No. 1 (1993), 1-5.
Honda, et al., "Inhibitory effects of 3-nitro-2,4,6-trihydroxybenzamides on . . . ", Cancer Letters, vol. 59, No. 2 (1991), 83-8.
Nakamura, et al., "Cancer chemopreventive effects of constituents of . . . ", Cancer Letters, vol. 177, No. 2 (2002), 119-24.
Yamaguchi, et al., "A Synthesis of Polyclicic Aromatic Compounds by the . . . ", J. Org. Chem., vol. 55, No. 5 (1990), 1611-23.
Kato, et al., "Studies on Keten and Its Derivatives. Part 89. Ethyl 4-Substituted Acetoacetates: Synthesis and Reaction with Diketen", Journal of the Chemical Society, vol. 2 (1979) 529-32.
Langer, et al., "Regioselective synthesis of functionalized homophthalates by cyclizations of 1,3-bis-(trimethylsiloxy)-1,3-butadienes with α-allenylesters", Tetrahedron Letters, vol. 41 (2000) 4545-47.
Inouye, et al., "Zwei Stark Bittere Glucoside Aus Swertia Japonica Makino: Amarogentin Und Amaroswerin", Tetrahedron Letters, vol. 9 (1968) 4919-24.
Chemical Abstract (of Inouye et al., Tetrahedron Letters, vol. 9 (1968) 4919-24), vol. 70 (1969) 11589v.

* cited by examiner

*Primary Examiner*—Shailendra Kumar
(74) *Attorney, Agent, or Firm*—Fitzpatrick, Cella, Harper & Scinto

(57) ABSTRACT

The present invention provides Hsp90 family protein inhibitors comprising, as an active ingredient, a benzoic acid derivative represented by General Formula (I):

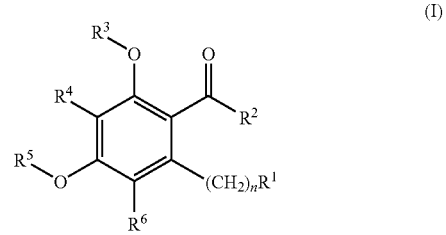

(I)

[wherein n represents an integer of 0 to 10; $R^1$ represents substituted or unsubstituted lower alkoxycarbonyl, substituted or unsubstituted aroyl, or the like; $R^2$ represents —$NR^{14}R^{15}$ (wherein $R^{14}$ and $R^{15}$ may be the same or different and each represents a hydrogen atom, substituted or unsubstituted lower alkyl, substituted or unsubstituted aralkyl or the like); $R^3$ and $R^5$ may be the same or different and each represents a hydrogen atom, substituted or unsubstituted lower alkyl or the like; and $R^4$ and $R^6$ may be the same or different and each represents a hydrogen atom, halogen, substituted or unsubstituted lower alkyl or the like] or a prodrug thereof, or a pharmaceutically acceptable salt of said benzoic acid derivative or said prodrug.

8 Claims, No Drawings

HSP90 FAMILY PROTEIN INHIBITORS

This application is a 371 of PCT/JP05/20519 Nov. 9, 2005.

TECHNICAL FIELD

The present invention relates to heat shock protein 90 (Hsp90) family protein inhibitors comprising, as an active ingredient, for example, a benzoic acid derivative or a prodrug thereof, or a pharmaceutically acceptable salt of said benzoic acid derivative or said prodrug, and the like.

BACKGROUND ART

As benzoic acid derivative, 2-benzoyloxymethyl-4,6-dihydroxybenzoic acid ethyl ester (refer to Non-patent Document 1), 3-ethyl-4,6-dihydroxy-2-methoxycarbonylmethylbenzoic acid methyl ester (refer to Non-patent Document 2), 3,5,3'-trihydroxybiphenyl-2-benzamide (refer to Non-patent Document 3) are known.

Benzoquinone ansamycin antibiotics such as Geldanamycin and Herbimycin, and Radicicol are known as compounds which bind to heat shock protein 90 (Hsp90) family proteins (Cell Stress & Chaperones, 1998, Vol. 3, p. 100-108; J. Med. Chem., 1999, Vol. 42, p. 260-266). Purine derivatives or pyrazole derivatives are also known as compounds which bind to Hsp90 family proteins (WO03/037860, WO03/055860). These compounds are all reported to bind to Hsp90 family proteins and inhibit the functions of Hsp90 family proteins, thereby exhibiting pharmacological activities such as anti-tumor activity. Therefore, compounds binding to Hsp90 family proteins are considered to be useful as therapeutic agents for diseases associated with Hsp90 family proteins or proteins to which Hsp90 family proteins bind (Hsp90 client proteins).

Examples of known Hsp90 family proteins include Hsp90α protein, Hsp90β protein, grp94 and hsp75/TRAP1 (Pharmacology & Therapeutics, 1998, Vol. 79, p. 129-168; Molecular Endocrinology, 1999, Vol. 13, p. 1435-1448; etc.).

Non-patent Document 1: Journal of the Chemical Society, Perkin Transactions 1, 1979, Vol. 2, p. 529-532

Non-patent Document 2: Tetrahedron Lett., 2000, Vol. 41, p. 4545-4947

Non-patent Document 3: Tetrahedron Lett., 1968, Vol. 8, p. 4919-4924

DISCLOSURE OF THE INVENTION

Problems to be Solved by the Invention

An object of the present invention is to provide Hsp90 family protein inhibitors comprising, as an active ingredient, for example, a benzoic acid derivative or a prodrug thereof, or a pharmaceutically acceptable salt of said benzoic acid derivative or said prodrug, and the like.

Means for Solving the Problems

The present invention relates to the following (1) to (49).

(1) A heat shock protein 90 (Hsp90) family protein inhibitor comprising, as an active ingredient, a benzoic acid derivative represented by General Formula (I):

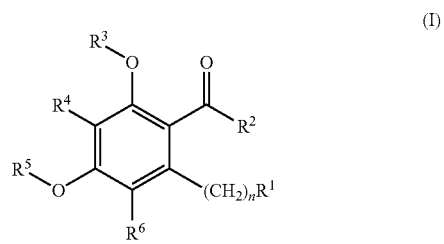

{wherein n represents an integer of 0 to 10;

$R^1$ represents a hydrogen atom, hydroxy, cyano, carboxy, nitro, formyl, halogen, substituted or unsubstituted lower alkyl, substituted or unsubstituted lower alkenyl, substituted or unsubstituted lower alkynyl, substituted or unsubstituted cycloalkyl, substituted or unsubstituted lower alkoxycarbonyl, substituted or unsubstituted aroyl, substituted or unsubstituted lower alkanoyl, substituted or unsubstituted heterocyclic alkyl, substituted or unsubstituted aryl, substituted or unsubstituted aralkyl, substituted or unsubstituted arylsulfonyl, a substituted or unsubstituted heterocyclic group, —CONR$^7$R$^8$ (wherein R$^7$ and R$^8$ may be the same or different and each represents a hydrogen atom, substituted or unsubstituted lower alkyl, substituted or unsubstituted cycloalkyl, substituted or unsubstituted lower alkanoyl, substituted or unsubstituted aryl, a substituted or unsubstituted heterocyclic group, substituted or unsubstituted aralkyl, substituted or unsubstituted heterocyclic alkyl, or substituted or unsubstituted aroyl, or R$^7$ and R$^8$ are combined together with the adjacent nitrogen atom thereto to form a substituted or unsubstituted heterocyclic group), —NR$^9$R$^{10}$ [wherein R$^9$ and R$^{10}$ may be the same or different and each represents a hydrogen atom, substituted or unsubstituted lower alkylsulfonyl, substituted or unsubstituted lower alkyl, substituted or unsubstituted cycloalkyl, substituted or unsubstituted lower alkanoly, substituted or unsubstituted aryl, a substituted or unsubstituted heterocyclic group, substituted or unsubstituted aralkyl, substituted or unsubstituted heterocyclic alkyl, substituted or unsubstituted aroyl or —CONR$^{11}$R$^{12}$ (wherein R$^{11}$ and R$^{12}$ have the same meanings as the above R$^7$ and R$^8$, respectively), or R$^9$ and R$^{10}$ are combined together with the adjacent nitrogen atom thereto to form a substituted or unsubstituted heterocyclic group] or —OR$^{13}$ (wherein R$^{13}$ represents substituted or unsubstituted lower alkyl, substituted or unsubstituted lower alkenyl, substituted or unsubstituted lower alkanoyl, substituted or unsubstituted aryl, a substituted or unsubstituted heterocyclic group, substituted or unsubstituted aralkyl, or substituted or unsubstituted heterocyclic alkyl);

$R^2$ represents —NR$^{14}$R$^{15}$ (wherein R$^{14}$ and R$^{15}$ may be the same or different and each represents a hydrogen atom, substituted or unsubstituted lower alkyl, substituted or unsubstituted cycloalkyl, substituted or unsubstituted lower alkanoyl, substituted or unsubstituted aryl, a substituted or unsubstituted heterocyclic group, substituted or unsubstituted aralkyl, substituted or unsubstituted heterocyclic alkyl, or substituted or unsubstituted aroyl or R$^{14}$ and R$^{15}$ are combined together with the adjacent nitrogen atom thereto to form a substituted or unsubstituted heterocyclic group) or —OR$^{16}$ (wherein R$^{16}$ represents substituted or unsubstituted lower alkyl, substituted or unsubstituted lower alkenyl, substituted or unsubstituted lower alkanoyl, substituted or unsubstituted aryl, a substituted or unsubstituted heterocyclic group, substituted or unsubstituted aralkyl, or substituted or unsubstituted heterocyclic alkyl);

$R^3$ and $R^5$ may be the same or different and each represents a hydrogen atom, carbamoyl, sulfamoyl, substituted or unsubstituted lower alkyl, substituted or unsubstituted lower alkenyl, substituted or unsubstituted lower alkanoyl, substituted or unsubstituted cycloalkyl, substituted or unsubstituted lower alkylsulfonyl, substituted or unsubstituted arylsulfonyl, lower alkylaminocarbonyl, di(lower alkyl)aminocarbonyl, substituted or unsubstituted lower alkoxycarbonyl, heterocyclic carbonyl, substituted or unsubstituted aralkyl, or substituted or unsubstituted aroyl; and $R^4$ and $R^6$ may be the same or different and each represents a hydrogen atom, hydroxy, halogen, cyano, nitro, formyl, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, amino, lower alkylamino, di(lower alkyl)amino, carboxy, substituted or unsubstituted lower alkoxycarbonyl, substituted or unsubstituted aryloxy, substituted or unsubstituted aryl, a substituted or unsubstituted heterocyclic group, substituted or unsubstituted lower alkanoyl, substituted or unsubstituted aroyl, substituted or unsubstituted aralkyl, or substituted or unsubstituted heterocyclic alkyl} or a prodrug thereof, or a pharmaceutically acceptable salt of said benzoic acid derivative or said prodrug.

(2) An Hsp90 family protein inhibitor comprising, as an active ingredient, a compound represented by General Formula (I):

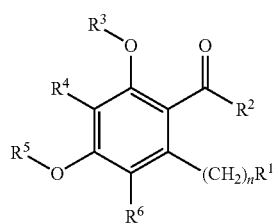

(wherein n, $R^1$, $R^2$, $R^3$, $R^4$, $R^5$ and $R^6$ have the same meanings as defined above, respectively) or a pharmaceutically acceptable salt thereof.

(3) The Hsp90 family protein inhibitor according to the above (1) or (2), wherein n is an integer of 1 to 10.

(4) The Hsp90 family protein inhibitor according to the above (1) or (2), wherein n is 1 or 2.

(5) The Hsp90 family protein inhibitor according to any of the above (1) to (4), wherein $R^1$ is hydroxy, substituted or unsubstituted lower alkyl, substituted or unsubstituted lower alkynyl, substituted or unsubstituted lower alkoxycarbonyl, —$CONR^7R^8$ (wherein $R^7$ and $R^8$ have the same meanings as defined above, respectively) or —$OR^{13}$ (wherein $R^{13}$ has the same meaning as defined above).

(6) The Hsp90 family protein inhibitor according to any of the above (1) to (4), wherein $R^1$ is hydroxy, substituted or unsubstituted lower alkoxycarbonyl, —$CONR^7R^8$ (wherein $R^7$ and $R^8$ have the same meanings as defined above, respectively) or —$OR^{13}$ (wherein $R^{13}$ has the same meaning as defined above).

(7) The Hsp90 family protein inhibitor according to the above (6), wherein $R^{13}$ is substituted or unsubstituted lower alkyl or substituted or unsubstituted aralkyl.

(8) The Hsp90 family protein inhibitor according to any of the above (1) to (7), wherein $R^2$ is —$NR^{14}R^{15}$ (wherein $R^{14}$ and $R^{15}$ have the same meanings as defined above, respectively).

(9) The Hsp90 family protein inhibitor according to any of the above (1) to (7), wherein $R^2$ is —$NR^{14a}R^{15a}$ (wherein $R^{14a}$ and $R^{15a}$ may be the same or different and each represents a hydrogen atom, substituted or unsubstituted lower alkyl, substituted or unsubstituted aralkyl, or substituted or unsubstituted heterocyclic alkyl or $R^{14a}$ and $R^{15a}$ are combined together with the adjacent nitrogen atom thereto to form a substituted or unsubstituted heterocyclic group).

(10) The Hsp90 family protein inhibitor according to any of the above (1) to (9), wherein $R^4$ is a hydrogen atom, hydroxy or halogen.

(11) The Hsp90 family protein inhibitor according to any of the above (1) to (10), wherein $R^3$ and $R^5$ may be the same or different and each is a hydrogen atom, sulfamoyl, substituted or unsubstituted lower alkyl, substituted or unsubstituted lower alkenyl, substituted or unsubstituted lower alkylsulfonyl, substituted or unsubstituted lower alkanoyl or substituted or unsubstituted aroyl.

(12) The Hsp90 family protein inhibitor according to any of the above (1) to (9), wherein $R^3$, $R^4$ and $R^5$ each is a hydrogen atom.

(13) The Hsp90 family protein inhibitor according to any of the above (1) to (12), wherein $R^6$ is a hydrogen atom, halogen, or lower alkyl.

(14) A benzoic acid derivative represented by General Formula (IA):

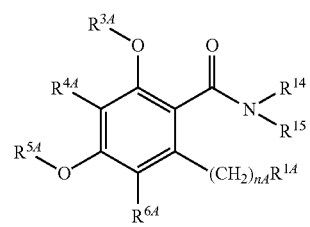

[wherein $R^{3A}$ and $R^{5A}$ may be the same or different and each represents a hydrogen atom, sulfamoyl, substituted or unsubstituted lower alkyl (excluding methyl), substituted or unsubstituted lower alkylsulfonyl, substituted or unsubstituted lower alkanoyl, substituted or unsubstituted aralkyl (excluding benzyl), or substituted or unsubstituted aroyl;

$R^{4A}$ represents a hydrogen atom, hydroxy or halogen;

$R^{6A}$ represents a hydrogen atom, halogen, cyano, nitro, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, substituted or unsubstituted lower alkanoyl, amino, lower alkylamino, di(lower alkyl)amino, carboxy, substituted or unsubstituted lower alkoxycarbonyl, substituted or unsubstituted aryloxy, substituted or unsubstituted aryl, a substituted or unsubstituted heterocyclic group, substituted or unsubstituted aralkyl, substituted or unsubstituted heterocyclic alkyl, or substituted or unsubstituted aroyl;

$R^{14}$ and $R^{15}$ have the same meanings as defined above, respectively;

nA represents an integer of 0 to 5;

[1] when nA is 0, $R^{14}$ represents cyano, carboxy, substituted or unsubstituted tert-butyl, substituted or unsubstituted isopropyl, substituted or unsubstituted lower alkenyl, substituted or unsubstituted lower alkynyl, substituted or unsubstituted cycloalkyl, substituted or unsubstituted lower alkanoyl, substituted or unsubstituted lower alkoxycarbonyl, substituted or unsubstituted aryl (excluding 3-hydroxyphenyl), substituted or unsubstituted aroyl, substituted or unsubstituted arylsulfonyl, a substituted or unsubstituted heterocyclic group, or —$CONR^7R^8$ (wherein $R^7$ and $R^8$ have the same meanings as defined above, respectively);

[2] when nA is an integer of 1 to 5, $R^{14}$ represents hydroxy, halogen, cyano, carboxy, substituted or unsubstituted lower alkyl, substituted or unsubstituted lower alkenyl, substituted or unsubstituted lower alkynyl, substituted or unsubstituted cycloalkyl, substituted or unsubstituted lower alkanoyl, substituted or unsubstituted lower alkoxycarbonyl, substituted or unsubstituted aryl, substituted or unsubstituted aroyl, substituted or unsubstituted heterocyclic alkyl, substituted or unsubstituted aralkyl, substituted or unsubstituted arylsulfonyl, a substituted or unsubstituted heterocyclic group, —$CONR^7R^8$ (wherein $R^7$ and $R^8$ have the same meanings as defined above, respectively), —$NR^9R^{10}$ (wherein $R^9$ and $R^{10}$ have the same meanings as defined above, respectively), or —$OR^{13}$ (wherein $R^{13}$ has the same meaning as defined above)]; or a pharmaceutically acceptable salt thereof.

(15) The benzoic acid derivative or a pharmaceutically acceptable salt thereof according to the above (14), wherein nA is an integer of 1 to 5.

(16) The benzoic acid derivative or a pharmaceutically acceptable salt thereof according to the above (14), wherein nA is 1 or 2.

(17) The benzoic acid derivative or a pharmaceutically acceptable salt thereof according to any of the above (14) to (16), wherein $R^{14}$ is hydroxy, substituted or unsubstituted lower alkyl, substituted or unsubstituted lower alkynyl, substituted or unsubstituted lower alkoxycarbonyl, —$CONR^7R^8$ (wherein $R^7$ and $R^8$ have the same meanings as defined above, respectively), or —$OR^{13}$ (wherein $R^{13}$ has the same meaning as defined above).

(18) The benzoic acid derivative or a pharmaceutically acceptable salt thereof according to any of the above (14) to (16), wherein $R^{14}$ is hydroxy, substituted or unsubstituted lower alkoxycarbonyl, —$CONR^7R^8$ (wherein $R^7$ and $R^8$ have the same meanings as defined above, respectively), or —$OR^{13}$ (wherein $R^{13}$ has the same meaning as defined above).

(19) The benzoic acid derivative or a pharmaceutically acceptable salt thereof according to the above (18), wherein $R^{13}$ is substituted or unsubstituted lower alkyl or substituted or unsubstituted aralkyl.

(20) The benzoic acid derivative or a pharmaceutically acceptable salt thereof according to any of the above (14) to (19), wherein $R^{14}$ and $R^{15}$ may be the same or different and each is a hydrogen atom, substituted or unsubstituted lower alkyl, substituted or unsubstituted aralkyl, or substituted or unsubstituted heterocyclic alkyl, or $R^{14}$ and $R^{15}$ are combined together with the adjacent nitrogen atom thereto to form a substituted or unsubstituted heterocyclic group.

(21) The benzoic acid derivative or a pharmaceutically acceptable salt thereof according to any of the above (14) to (20), wherein $R^{4A}$ is a hydrogen atom.

(22) The benzoic acid derivative or a pharmaceutically acceptable salt thereof according to any of the above (14) to (21), wherein $R^{3A}$ and $R^{5A}$ may be the same or different and each is a hydrogen atom, sulfamoyl, substituted or unsubstituted lower alkylsulfonyl, substituted or unsubstituted lower alkanoyl, or substituted or unsubstituted aroyl.

(23) The benzoic acid derivative or a pharmaceutically acceptable salt thereof according to any of the above (14) to (20), wherein $R^{3A}$, $R^{4A}$, and $R^{5A}$ each is a hydrogen atom.

(24) The benzoic acid derivative or a pharmaceutically acceptable salt thereof according to any of the above (14) to (23), wherein $R^{6A}$ is a hydrogen atom, halogen, or substituted or unsubstituted lower alkyl.

(25) A benzoic acid derivative represented by General Formula (IB):

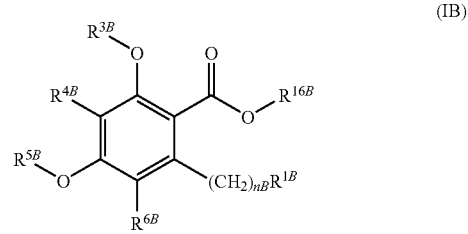

(IB)

[wherein $R^{3B}$ and $R^{5B}$ may be the same or different and each represents a hydrogen atom, sulfamoyl, substituted or unsubstituted lower alkylsulfonyl, substituted or unsubstituted lower alkanoyl, or substituted or unsubstituted aroyl;

$R^{4B}$ represents a hydrogen atom, hydroxyl, or halogen;

$R^{6B}$ represents a hydrogen atom, halogen, cyano, nitro, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, substituted or unsubstituted lower alkanoyl, amino, lower alkylamino, di(lower alkyl)amino, carboxy, substituted or unsubstituted lower alkoxycarbonyl, substituted or unsubstituted aryloxy, substituted or unsubstituted aralkyl, or substituted or unsubstituted heterocyclic alkyl;

$R^{16B}$ represents substituted or unsubstituted lower alkyl, substituted or unsubstituted lower alkenyl, substituted or unsubstituted lower alkanoyl, substituted or unsubstituted aryl (excluding substituted phenyl), a substituted or unsubstituted heterocyclic group (excluding substituted or unsubstituted 1-oxoisochroman-6-yl), substituted or unsubstituted aralkyl (excluding benzyl and 4-nitrobenzyl), or substituted or unsubstituted heterocyclic alkyl;

nB represents an integer of 0 to 5

[1] when nB is 0, $R^{1B}$ represents cyano, carboxy, substituted or unsubstituted tert-butyl, substituted or unsubstituted isopropyl, substituted lower alkenyl (excluding substituted vinyl), substituted or unsubstituted lower alkynyl, substituted or unsubstituted cycloalkyl, substituted or unsubstituted lower alkanoyl (excluding pentanoyl), substituted or unsubstituted lower alkoxycarbonyl (excluding methoxycarbonyl), substituted or unsubstituted aroyl, substituted or unsubstituted heterocyclic alkyl, substituted or unsubstituted aralkyl, substituted or unsubstituted arylsulfonyl, or —CONR$^7$R$^8$ (wherein R$^7$ and R$^8$ have the same meanings as defined above, respectively),

[2] when nB represents an integer of 1 to 5, $R^{1B}$ represents cyano, substituted or unsubstituted lower alkynyl, substituted or unsubstituted cycloalkyl, substituted or unsubstituted lower alkoxycarbonyl, substituted or unsubstituted aryl (excluding substituted or unsubstituted phenyl), substituted or unsubstituted aroyl, substituted or unsubstituted heterocyclic alkyl, substituted or unsubstituted arylsulfonyl, a substituted or unsubstituted heterocyclic group (excluding substituted or unsubstituted 1,3-dioxolanyl and substituted or unsubstituted 4-oxochromen-2-yl), —CONR$^7$R$^8$ (wherein R$^7$ and R$^8$ have the same meanings as defined above, respectively), —NR$^9$R$^{10}$ (wherein R$^9$ and R$^{10}$ have the same meanings as defined above, respectively), or —OR$^{13b}$ (wherein R$^{13b}$ represents substituted or unsubstituted lower alkyl, substituted or unsubstituted lower alkenyl, substituted or unsubstituted lower alkanoyl, substituted or unsubstituted aryl, a substituted or unsubstituted heterocyclic group, substituted or unsubstituted aralkyl, or substituted or unsubstituted heterocyclic alkyl), provided that (i) when $R^{16B}$ is ethyl, —(CH$_2$)$_{nB}$R$^{1B}$ is not a group selected from a group consisting of benzyloxymethyl, phenyloxymethyl, and ethoxymethyl, (ii) when $R^{16B}$ is methyl, —(CH$_2$)$_{nB}$R$^{1B}$ is not methoxycarbonylmethyl] or a pharmaceutically acceptable salt thereof.

(26) The benzoic acid derivative or a pharmaceutically acceptable salt thereof according to the above (25), wherein nB is an integer of 1 to 5.

(27) The benzoic acid derivative or a pharmaceutically acceptable salt thereof according to the above (25), wherein nB is 1 or 2.

(28) The benzoic acid derivative or a pharmaceutically acceptable salt thereof according to any of the above (25) to (27), wherein $R^{1B}$ is —OR$^{13b}$ (wherein R$^{13b}$ have the same meanings as defined above).

(29) The benzoic acid derivative or a pharmaceutically acceptable salt thereof according to the above (28), wherein R$^{13b}$ is substituted or unsubstituted aralkyl.

(30) The benzoic acid derivative or a pharmaceutically acceptable salt thereof according to any of the above (25) to (29), wherein $R^{16B}$ is substituted or unsubstituted lower alkyl.

(31) The benzoic acid derivative or a pharmaceutically acceptable salt thereof according to any of the above (25) to (30), wherein $R^{4B}$ is a hydrogen atom.

(32) The benzoic acid derivative or a pharmaceutically acceptable salt thereof according to any of the above (25) to (30), wherein $R^{3B}$, $R^{4B}$ and $R^{5B}$ each is a hydrogen atom.

(33) The benzoic acid derivative or a pharmaceutically acceptable salt thereof according to any of the above (25) to (32), wherein $R^{6B}$ is a hydrogen atom, halogen or substituted or unsubstituted lower alkyl.

(34) A pharmaceutical composition comprising, as an active ingredient, the benzoic acid derivative according to any of the above (14) to (33) or a prodrug thereof, or a pharmaceutically acceptable salt of said benzoic acid derivative or said prodrug.

(35) A pharmaceutical composition comprising, as an active ingredient, the benzoic acid derivative according to any of the above (14) to (33) or a pharmaceutically acceptable salt thereof.

(36) An Hsp90 family protein inhibitor comprising, as an active ingredient, the benzoic acid derivative according to any of the above (14) to (33) or a prodrug thereof, or a pharmaceutically acceptable salt of said benzoic acid derivative or said prodrug.

(37) An Hsp90 family protein inhibitor comprising, as an active ingredient, the benzoic acid derivative according to any of the above (14) to (33) or a pharmaceutically acceptable salt thereof.

(38) A therapeutic agent for diseases associated with Hsp90 family proteins or proteins to which Hsp90 family proteins bind (Hsp90 client proteins) comprising, as an active ingredient, the benzoic acid derivative according to any of the above (14) to (33) or a prodrug thereof, or a pharmaceutically acceptable salt of said benzoic acid derivative or said prodrug.

(39) A therapeutic agent for diseases associated with Hsp90 family proteins or proteins to which Hsp90 family proteins bind (Hsp90 client proteins) comprising, as an active ingredient, the benzoic acid derivative according to any of the above (14) to (33) or a pharmaceutically acceptable salt thereof.

(40) An antitumor agent comprising, as an active ingredient, the benzoic acid derivative according to any of the above (14) to (33) or a prodrug thereof, or a pharmaceutically acceptable salt of said benzoic acid derivative or said prodrug.

(41) An antitumor agent comprising, as an active ingredient, the benzoic acid derivative according to any of the above (14) to (33) or a pharmaceutically acceptable salt thereof.

(42) A method for inhibiting heat shock protein 90 (Hsp90) family protein comprising administering an effective amount of a compound represented by General Formula (I):

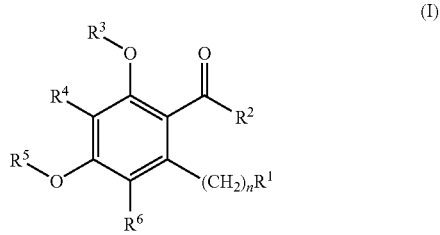

(wherein n, R$^1$, R$^2$, R$^3$, R$^4$, R$^5$, and R$^6$ have the same meanings as defined above, respectively) or a prodrug thereof, or a pharmaceutically acceptable salt of said compound or said prodrug.

(43) A method for inhibiting Hsp90 family protein comprising administering an effective amount of the benzoic acid derivative according to any of the above (14) to (33) or a prodrug thereof, or a pharmaceutically acceptable salt of said benzoic acid derivative or said prodrug.

(44) A method for treating diseases associated with Hsp90 family proteins or proteins to which Hsp90 family proteins bind (Hsp90 client proteins) comprising administering an effective amount of the benzoic acid derivative according to any of the above (14) to (33) or a prodrug thereof, or a pharmaceutically acceptable salt of said benzoic acid derivative or said prodrug.

(45) A method for treating malignant tumor comprising administering an effective amount of the benzoic acid derivative according to any of the above (14) to (33) or a prodrug thereof, or a pharmaceutically acceptable salt of said benzoic acid derivative or said prodrug.

(46) Use of a compound represented by General Formula (I):

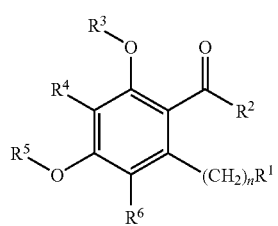

(wherein n, $R^1$, $R^2$, $R^3$, $R^4$, $R^5$, and $R^6$ have the same meanings as defined above, respectively) or a prodrug thereof, or a pharmaceutically acceptable salt of said compound or said prodrug for the manufacture of heat shock protein 90 (Hsp90) family protein inhibitor.

(47) Use of the benzoic acid derivative according to any of the above (14) to (33) or a prodrug thereof, or a pharmaceutically acceptable salt of said benzoic acid derivative or said prodrug for the manufacture of heat shock protein 90 (Hsp90) family protein inhibitor.

(48) Use of the benzoic acid derivative according to any of the above (14) to (33) or a prodrug thereof, or a pharmaceutically acceptable salt of said benzoic acid derivative or said prodrug for the manufacture of therapeutic agent for diseases associated with Hsp90 family proteins or proteins to which Hsp90 family proteins bind (Hsp90 client proteins).

(49) Use of the benzoic acid derivative according to any of the above (14) to (33) or a prodrug thereof, or a pharmaceutically acceptable salt of said benzoic acid derivative or said prodrug for the manufacture of antitumor agent.

Effect of the Invention

The present invention provides, for example, Hsp90 family protein inhibitors comprising, as an active ingredient, a benzoic acid derivative or a prodrug thereof, or a pharmaceutically acceptable salt of said benzoic acid derivative or said prodrug, and the like.

BEST MODE FOR CARRYING OUT THE INVENTION

In the definitions of the groups in General Formula (I), (IA) and (IB):
Examples of the lower alkyl moiety of the lower alkyl, lower alkoxy, lower alkoxycarbonyl, lower alkylsulfonyl, lower alkylaminocarbonyl, di(lower alkyl)aminocarbonyl, lower alkylamino and di(lower alkyl)amino include straight-chain or branched alkyl groups having 1 to 8 carbon atoms, such as methyl, ethyl, propyl, isopropyl, butyl, sec-butyl, tert-butyl, pentyl, isopentyl, neopentyl, hexyl, heptyl and octyl. The two lower alkyl moieties of the di(lower alkyl) amino and di(lower alkyl)aminocarbonyl may each be the same or different.

Examples of the lower alkenyl include straight-chain or branched alkenyl having 2 to 8 carbon atoms, such as vinyl, allyl, propa-1-en-yl, isopropenyl, crotyl, buta-1-en-1-yl, buta-2-en-1-yl, buta-3-en-1-yl, penta-2-en-1-yl, 3-methylbuta-1-en-1-yl, 3-methylbuta-2-en-1-yl, penta-4-en-1-yl, hexa-2-en-1-yl, hexa-5-en-1-yl, hepta-2-en-1-yl, and octa-2-en-1-yl.

Examples of the lower alkynyl include straight-chain or branched alkynyl having 2 to 8 carbon atoms, such as ethynyl, propynyl, butynyl, pentynyl, hexynyl, heptynyl and octynyl.

Examples of the lower alkanoyl include straight-chain or branched alkanoyl having 2 to 7 carbon atoms, such as acetyl, propionyl, butyryl, isobutyryl, valeryl, isovaleryl, pivaloyl, hexanoyl and heptanoyl.

Examples of the cycloalkyl include cycloalkyl having 3 to 8 carbon atoms, such as cyclopropyl, cyclobutyl, cyclopentyl, cyclohexyl, cycloheptyl and cyclooctyl.

Examples of the aryl moiety of the aryl, arylsulfonyl, aryloxy and aroyl include monocyclic, bicyclic or tricyclic aryl having 6 to 14 carbon atoms, such as phenyl, indenyl, naphthyl and anthryl.

Examples of the aralkyl include aralkyl having 7 to 15 carbon atoms, such as benzyl, phenethyl, benzhydryl and naphthylmethyl.

Examples of the heterocyclic moiety of the heterocyclic group, heterocyclic alkyl and heterocyclic carbonyl include aromatic heterocyclic group, aliphatiic heterocyclic group and the like.

Examples of the aromatic heterocyclic group include 5- or 6-membered monocyclic aromatic heterocyclic groups containing at least one atom selected from a nitrogen atom, an oxygen atom and a sulfur atom, and bicyclic or tricyclic condensed-ring aromatic heterocyclic groups containing at least one atom selected from a nitrogen atom, an oxygen atom and a sulfur atom in which 3- to 8-membered rings are condensed, such as pyridyl, pyrazinyl, pyrimidinyl, pyridazinyl, quinolinyl, isoquinolinyl, phthalazinyl, quinazolinyl, quinoxalinyl, naphthyridinyl, cinnolinyl, pyrrolyl, pyrazolyl, imidazolyl, triazolyl, tetrazolyl, thienyl, furyl, thiazolyl, isothiazolyl, oxazolyl, isoxazolyl, oxadiazolyl, thiadiazolyl, indolyl, indazolyl, benzimidazolyl, benzotriazolyl, benzothiazolyl, benzoxazolyl, purinyl, dibenzofuranyl and 4-oxochromen-2-yl.

Examples of the aliphatic heterocyclic group include 5- or 6-membered monocyclic aliphatic heterocyclic groups containing at least one atom selected from a nitrogen atom, an oxygen atom and a sulfur atom, and bicyclic or tricyclic condensed-ring aliphatic heterocyclic groups containing at least one atom selected from a nitrogen atom, an oxygen atom and a sulfur atom in which 3- to 8-membered rings are condensed, such as pyrrolidinyl, piperidino, piperidyl, piperazinyl, morpholino, morpholinyl, thiomorpholino, thiomorpholinyl, homopiperidino, homopiperidyl, homopiperazinyl, tetrahydropyridinyl, tetrahydroquinolinyl, tetrahydroisoquinolinyl, oxazolinyl, oxazolidinyl, oxooxazolidinyl, oxadiazolinyl, oxiranyl, tetrahydrofuranyl, tetrahydropyranyl, dihydrobenzofuranyl, oxopiperazinyl, oxooxadiazolinyl, 2-oxopyrrolidinyl dioxolanyl, benzodioxolyl, benzodioxanyl, benzopyranyl, and 1-oxoisochroman-6-yl.

Examples of the heterocyclic group formed together with the adjacent nitrogen atom include 5- or 6-membered monocyclic heterocyclic groups containing at least one nitrogen atom (the monocyclic heterocyclic groups may also contain another nitrogen atom, an oxygen atom or a sulfur atom), and bicyclic or tricyclic condensed-ring heterocyclic groups containing at least one nitrogen atom in which 3- to 8-membered rings are condensed (the condensed-ring heterocyclic groups may also contain another nitrogen atom, an oxygen atom or a sulfur atom), such as pyrrolidinyl, piperidino, piperazinyl, morpholino, thiomorpholino, homopiperidino, homopiperazinyl, tetrahydropyridinyl, tetrahydroquinolinyl, and tetrahydroisoquinolinyl.

The alkylene moiety of the heterocyclic alkyl has the same meaning as a group produced by removing one hydrogen atom from the above-described lower alkyl.

The halogen means fluorine, chlorine, bromine and iodine atoms.

Examples of the substituents (A) in the substituted lower alkyl, substituted tert-butyl, substituted isopropyl, substituted lower alkoxy, substituted lower alkoxycarbonyl, substituted lower alkylsulfonyl, substituted lower alkanoyl, substituted lower alkenyl, substituted lower alkynyl and substituted vinyl include 1 to 3 substituents which may be the same or different, such as hydroxy, cyano, nitro, carboxy, carbamoyl, amino, hydroxyimino, lower alkoxyimino, halogen, substituted or unsubstituted lower alkoxy, cycloalkyl, lower alkanoyl, lower alkoxycarbonyl, substituted or unsubstituted lower alkylaminocarbonyl, substituted or unsubstituted di(lower alkyl)aminocarbonyl, lower alkylamino, di(lower alkyl)amino, and substituted or unsubstituted lower alkanoylamino. The position(s) to be substituted by the substituent(s) is/are not particularly limited.

The halogen, lower alkoxy, cycloalkyl, lower alkanoyl, lower alkoxycarbonyl, lower alkylaminocarbonyl, di(lower alkyl)aminocarbonyl, lower alkylamino and di(lower alkyl)amino described as examples of substituents (A) each have the same meanings as defined above. The lower alkoxy moiety of the lower alkoxyimino has the same meaning as the above lower alkoxy and the lower alkanoyl moiety of the lower alkanoylamino has the same meaning as the above lower alkanoyl.

Examples of the substituents (a) in the substituted lower alkoxy, substituted lower alkylaminocarbonyl, substituted di(lower alkyl)aminocarbonyl and substituted lower alkanoylamino described as an example of substituent (A) include 1 to 3 substituents which may be the same or different, such as hydroxy, halogen and lower alkoxy and the halogen and the lower alkoxy described as examples of substituent (a) each have the same meanings as defined above.

Examples of substituents (B) in the substituted cycloalkyl, substituted aryl, substituted phenyl, substituted arylsulfonyl, substituted aryloxy, substituted aralkyl, substituted aroyl, substituted heterocyclic group, substituted 1,3-dioxolanyl, substituted 1-oxoisochroman-6-yl, substituted 4-oxochromen-2-yl, substituted heterocyclic alkyl, and substituted heterocyclic group combined together with the adjacent nitrogen atom thereto include 1 to 3 substituents which may be the same or different, such as hydroxy, halogen, nitro, cyano, amino, carboxy, carbamoyl, substituted or unsubstituted lower alkyl, substituted or unsubstituted lower alkoxy, aralkyloxy, lower alkylsulfonyl, cycloalkyl, lower alkoxycarbonyl, heterocyclic carbonyl, lower alkylamino, di-lower alkylamino, lower alkanoyl, substituted or unsubstituted heterocyclic group, substituted or unsubstituted heterocyclic alkyl, and substituted or unsubstituted aryl. The position(s) to be substituted by the substituent(s) is/are not particularly limited.

The halogen, lower alkyl, lower alkoxy, lower alkylsulfonyl, cycloalkyl, lower alkoxycarbonyl, lower alkylamino, di(lower alkyl)amino, lower alkanoyl, heterocyclic group, heterocyclic alkyl, heterocyclic carbonyl, and aryl described as examples of substituent (B) have the same meanings as defined above, respectively. The aralkyl moiety of the aralkyloxy has the same meaning as the above aralkyl.

Examples of the substituents in the substituted lower alkyl and the substituted lower alkoxy described as examples of substituent (B) include, for example, substituents similar to the group described as an example of substituent (a) and the like. Examples of the substituents (b) in the substituted heterocyclic group, substituted heterocyclic alkyl and substituted aryl described as examples of substituent (B) include 1 to 3 substituents which may be the same or different, such as hydroxy, cyano, halogen, lower alkyl, and lower alkoxy. The halogen, lower alkyl and lower alkoxy described as examples of substituent (b) each have the same meanings as defined above.

Hereinafter, the compound represented by General Formula (I) is referred to as Compound (I), and the same applies to compounds of other formula numbers.

The prodrugs of Compound (I) include compound which is converted in vivo, for example, by various mechanisms such as hydrolysis in blood to form Compound (I) of the present invention, and the like. Such compound can be specified by techniques well known in the art (e.g. J. Med. Chem., 1997, Vol. 40, p. 2011-2016; Drug Dev. Res., 1995, Vol. 34, p. 220-230; Advances in Drug Res., 1984, Vol. 13, p. 224-331; Bundgaard, Design of Prodrugs, 1985, Elsevier Press and the like).

Specifically, when Compound (I) has carboxy in its structure, examples of prodrugs of Compound (I) include compounds in which the hydrogen atom of said carboxy is substituted with a group selected from lower alkyl, lower alkanoyloxyalkyl [e.g. lower alkanoyloxymethyl, 1-(lower alkanoyloxy)ethyl and 1-methyl-1-(lower alkanoyloxy)ethyl], lower alkoxycarbonyloxyalkyl [e.g. lower alkoxycarbonyloxymethyl, 1-(lower alkoxycarbonyloxy)ethyl, and 1-methyl-1-(lower alkoxycarbonyloxy)ethyl], N-(lower alkoxycarbonyl)aminoalkyl {e.g. N-(lower alkoxycarbonyl) aminomethyl and 1-[N-(lower alkoxycarbonyl)amino] ethyl}, 3-phthalidyl, 4-crotonolactonyl, γ-butyrolacton-4-yl, di(lower alkyl)aminoalkyl, carbamoylalkyl, di(lower alkyl) carbamoylalkyl, piperidinoalkyl, pyrrolidinoalkyl, morpholinoalkyl and the like.

Also, when Compound (I) has alcoholic hydroxy in its structure, examples of prodrugs of Compound (I) include compounds in which the hydrogen atom of said hydroxy is substituted with a group selected from lower alkanoyloxyalkyl, 1-(lower alkanoyloxy)ethyl, 1-methyl-1-(lower alkanoyloxy)ethyl, lower alkoxycarbonyloxyalkyl, N-(lower alkoxycarbonyl)aminoalkyl, succinoyl, lower alkanoyl, α-amino lower alkanoyl and the like.

Also, when Compound (I) has amino in its structure, examples of prodrugs of Compound (I) include compounds in which one or two hydrogen atoms of said amino are substituted with a group selected from lower alkylcarbonyl, lower alkoxycarbonyl, lower alkylcarbamoyl, di(lower alkyl)carbamoyl and the like.

The lower alkyl moiety of the above-described lower alkyl, lower alkoxycarbonyloxyalkyl, lower alkoxycarbonyloxymethyl, 1-(lower alkoxycarbonyloxy)ethyl, 1-methyl-1-(lower alkoxycarbonyloxy)ethyl, N-(lower alkoxycarbonyl)aminoalkyl, N-(lower alkoxycarbonyl)aminomethyl, 1-[N-(lower alkoxycarbonyl)amino]ethyl, di(lower alkyl)aminoalkyl, di(lower alkyl)carbamoylalkyl, lower alkoxycarbonyloxymethyl, N-lower alkoxycarbonylaminomethyl, lower alkylcarbonyl, lower alkoxycarbonyl, lower alkylcarbamoyl and di(lower alkyl)carbamoyl has the same meaning as the above-described lower alkyl. The two lower alkyl moieties of the di(lower alkyl)aminoalkyl, di(lower alkyl)carbamoylalkyl and di(lower alkyl)carbamoyl each may be the same or different.

Also, the lower alkanoyl moiety of the above-described lower alkanoyloxyalkyl, lower alkanoyloxymethyl, 1-(lower alkanoyloxy)ethyl, 1-methyl-1-(lower alkanoyloxy)ethyl, lower alkanoyl and α-amino lower alkanoyl has the same meaning as the above-described lower alkanoyl.

Also, the alkylene moiety of the above-described lower alkanoyloxyalkyl, lower alkoxycarbonyloxyalkyl, N-(lower alkoxycarbonyl)aminoalkyl, di(lower alkyl)aminoalkyl, carbamoylalkyl, di(lower alkyl)carbamoylalkyl, piperidinoalkyl, pyrrolidinoalkyl and morpholinoalkyl has the same meaning as the group formed by removing a hydrogen atom from the above-described lower alkyl.

These prodrugs of Compound (I) can be prepared from Compound (I) according to, for example, the methods described in T. W. Greene, Protective Groups in Organic Synthesis, third edition, John Wiley & Sons Inc. (1999), or methods similar thereto.

A pharmaceutically acceptable salt of Compound (I) or a prodrug thereof include pharmaceutically acceptable acid addition salt, metal salt, ammonium salt, organic amine addition salt and amino acid addition salt.

Examples of the pharmaceutically acceptable acid addition salt of Compound (I) or a prodrug thereof include inorganic acid salts such as hydrochloride, sulfate, nitrate and phosphate, and organic acid salts such as acetate, maleate, fumarate and citrate. Examples of the pharmaceutically acceptable metal salts include alkali metal salts such as sodium salt and potassium salt, alkaline earth metal salts such as magnesium salt and calcium salt, aluminum salt, and zinc salt. Examples of the pharmaceutically acceptable ammonium salts include ammonium and tetramethylammonium. Examples of the pharmaceutically acceptable organic amine addition salts include an addition salt of morpholine or piperidine. Examples of the pharmaceutically acceptable amino acid addition salts include an addition salt of glycine, phenylalanine, lysine, aspartic acid or glutamic acid.

The term "inhibition of Hsp90 family protein" refers to inhibition of the binding of Hsp90 family protein to a protein to which Hsp90 family protein binds (Hsp90 client protein).

Examples of Hsp90 family proteins include Hsp90α protein, Hsp90β protein, grp94 and hsp75/TRAP1.

The proteins to which Hsp90 family proteins bind include any proteins to which Hsp90 family proteins bind, for example, EGFR, Erb-B2, Bcr-Abl, src, raf-1, AKT, Flt-3, PLK, Wee1, FAK, cMET, hTERT, HIF1-α, mutant p53, estrogen receptors and androgen receptors (Expert Opinion on Biological Therapy, 2002, Vol. 2, p. 3-24).

The production method of Compound (I) are described below.

In the processes shown below, when the defined groups undergo changes under the reaction conditions or are not suitable to carry out the processes, production can be easily performed by applying means generally used in synthetic organic chemistry, such as protection of functional groups, removal of protecting groups and the like [e.g. T. W. Greene, Protective Groups in Organic Synthesis, third edition, John Wiley & Sons Inc. (1999)]. If necessary, the order of reaction steps such as introduction of a substituent may be changed.

Compound (I) or a intermediate thereof can be obtained, for example, according to Production Methods shown below and the like.

Production Method 1:

Compound (I) can be produced according to the following step.

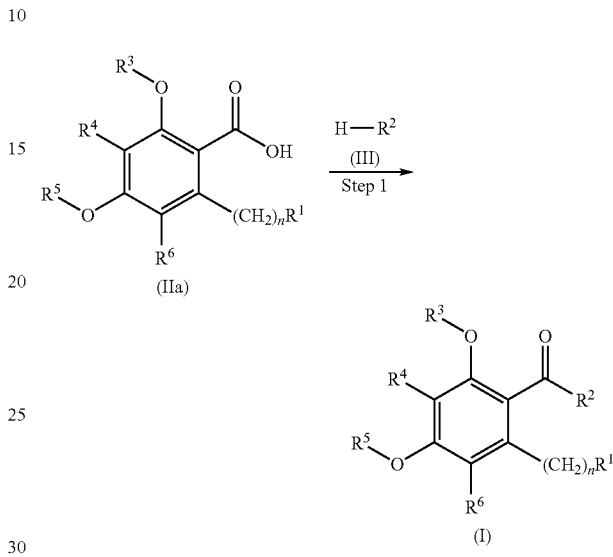

(wherein $R^1$ to $R^6$ and n have the same meanings as defined above, respectively)

(Step 1)

Compound (I) can be obtained by condensation reaction of Compound (IIa) and Compound (III).

For example, Compound (I) can be obtained by reacting Compound (IIa) with Compound (III) in a solvent in the presence of an activator such as 1-hydroxybenzotriazole or N-hydroxysuccinimide and a condensing agent. If necessary, 1 to 20 equivalents of a base may be added thereto when the reaction is carried out. In general, the condensing agent, the activator and Compound (III) are each used in an amount of 1 to 20 equivalents based on Compound (IIa), and the reaction is carried out at a temperature between −20° C. and the boiling point of the solvent used for 1 minute to 24 hours.

Examples of the solvent include halogenated hydrocarbons such as dichloromethane and chloroform; esters such as methyl acetate, ethyl acetate and isobutyl acetate; ethers such as diethylether, tetrahydrofuran and 1,4-dioxane; aromatic hydrocarbons such as benzene and toluene; acetonitrile; N,N-dimethylformamide; N-methylpiperidone; and mixtures thereof.

Examples of the condensing agent include dicyclohexylcarbodiimide, 1-[3-(dimethylamino)propyl]-3-ethylcarbodiimide hydrochloride, polymer-bound 1-[3-(dimethylamino)propyl]-3-ethylcarbodiimide and triphenylphosphine oxide•trifluoromethanesulfonic anhydride.

Examples of the base include alkylamines such as triethylamine, diisopropyl ethylamine and N-methylmorpholine; pyridines such as pyridine, lutidine, collidine and 4-dimethylaminopyridine; alkali metal carbonates such as potassium carbonate and sodium hydrogencarbonate; and alkali metal hydroxides such as potassium hydroxide, sodium hydroxide and lithium hydroxide.

Prior to use in the reaction, Compound (IIa) may be treated with the activator, or the carboxyl group of Compound (IIa) may be converted to a highly reactive group such as chlorocarbonyl, bromocarbonyl, p-nitrophenoxycarbonyl, pentafluorophenoxycarbonyl or pentafluorothiophenoxycarbonyl.

Starting material, Compound (III) can be obtained as a commercially available product or according to a known method [e.g. R. C. Larock, Comprehensive Organic Transformations, second edition, John Wiley & Sons Inc. (1999)] or methods similar thereto. Compound (IIa), which is a raw material, can be obtained according to a known method (e.g. J. Am. Chem. Soc., 1971, Vol. 93, p. 6708-6709) or methods similar thereto such as the following Starting Material Production Method 1.

Starting Material Production Method 1:

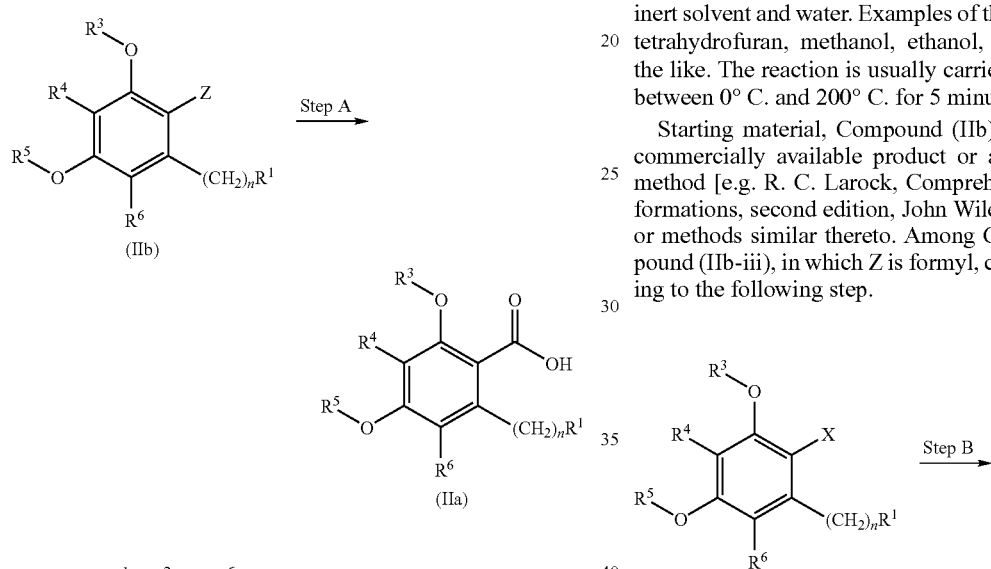

[wherein $R^1$, $R^3$ to $R^6$ and n have the same meanings as defined above, respectively; and Z represents halogen (the halogen has the same meaning as defined above), formyl, hydroxymethyl or methyl]

(Step A)

When Z is formyl, hydroxymethyl or methyl:

Compound (IIa) can be obtained by treating Compound (IIb-i), i.e. Compound (IIb) in which Z is formyl, hydroxymethyl or methyl, with 1 to 20 equivalents of an oxidizing agent such as sodium chlorite, potassium dichromate, and potassium permaganate in an inert solvent. Examples of the inert solvent include dichloromethane, chloroform, tetrahydrofuran, N,N-dimethylformamide, tert-butyl alcohol, water, mixed solvent thereof and the like. The reaction is usually carried out at a temperature between 0° C. and 50° C. for 5 minutes to 24 hours.

When Z is halogen:

Compound (IIa) can be obtained by treating Compound (IIb-ii), i.e. Compound (IIb) in which Z is halogen, with 1 to 5 equivalents of an organometallic compound such as n-butyllithium, sec-butyllithium, tert-butyllithium, and lithiumdiisopropylamide, or metal such as magnesium and zinc in an inert solvent, followed by treating with 1 to 100 equivalents of carbon dioxide. Examples of the inert solvent include tetrahydrofuran, diethylether, toluene, a mixed solvent thereof and the like. The reaction is usually carried out at a temperature between −78° C. and 50° C. for 5 minutes to 24 hours.

Also, Compound (IIa) can be obtained by treating Compound (IIb-ii) with 1 to 5 equivalents of acid such as formic acid, acetic acid, and ammonium formate and 1 to 100 equivalents of carbon monoxide in an inert solvent, in the presence of 0.001 to 2 equivalents of transition metal catalyst. Examples of the inert solvent include tetrahydrofuran, diethylether, toluene, a mixed solvent thereof and the like. Examples of the transition metal catalyst include palladium chloride, tetrakis(triphenylphosphine)palladium, palladium acetate and the like. The reaction is usually carried out at a temperature between 0° C. and 200° C. for 5 minutes to 72 hours.

Also, Compound (IIa) can be obtained by treating Compound (I) in which $R^2$ is substituted or unsubstituted lower alkoxy or substituted or unsubstituted aryloxy with 1 to 5 equivalents of base such as sodium hydroxide, lithium hydroxide, and potassium hydroxide in a mixed solvent of inert solvent and water. Examples of the inert solvent include tetrahydrofuran, methanol, ethanol, dichloromethane, and the like. The reaction is usually carried out at a temperature between 0° C. and 200° C. for 5 minutes to 24 hours.

Starting material, Compound (IIb) can be obtained as a commercially available product or according to a known method [e.g. R. C. Larock, Comprehensive Organic Transformations, second edition, John Wiley & Sons Inc. (1999)] or methods similar thereto. Among Compound (IIb), Compound (IIb-iii), in which Z is formyl, can be obtained according to the following step.

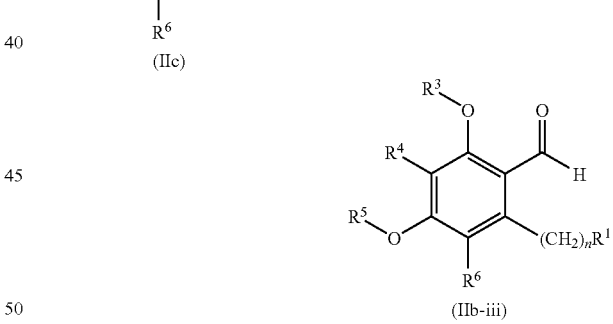

[wherein $R^1$, $R^3$ to $R^6$, and n have the same meanings as defined above, respectively, X represents halogen (the halogen has the same meaning as defined above)]

(Step B)

Compound (IIb-iii) can be obtained by treating Compound (IIc) with 1 to 5 equivalents of organometallic compound such as n-butyllithium, sec-butyllithium, tert-butyllithium, and lithiumdiisopropylamide, or metal such as magnesium and zinc in an inert solvent, followed by treating with formylating agent such as N,N-dimethylformamide, and N-formylmorpholine. Examples of the inert solvent include tetrahydrofuran, diethylether, toluene, and the like. The reaction is usually carried out at a temperature between −78° C. and 50° C. for 5 minutes to 24 hours.

Starting material, Compound (IIc) can be obtained as a commercially available product or according to a known method [e.g. R. C. Larock, Comprehensive Organic Transformations, second edition, John Wiley & Sons Inc. (1999)] or methods similar thereto such as the following step.

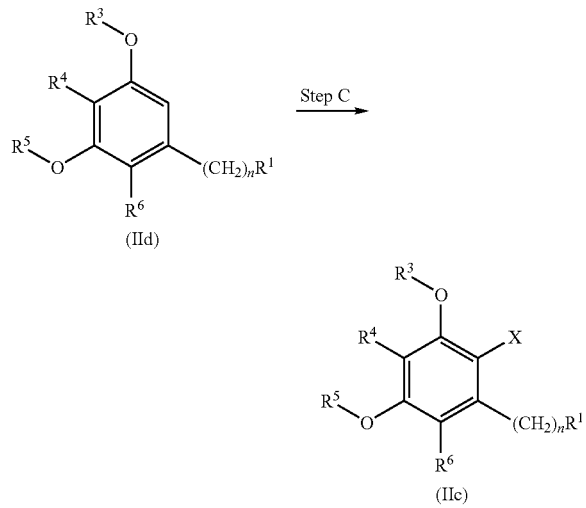

(wherein $R^1$, $R^3$ to $R^6$, n and X have the same meanings as defined above, respectively)

(Step C)

Compound (IIc) can be obtained by treating Compound (IId) with 1 to 2 equivalents of corresponding halogenating agent such as N-bromosuccinimide, N-chlorosuccinimide, chlorine, bromine, iodine, and a combination of iodine and [bis(trifluoroacetoxy)iodo]benzene in an inert solvent. Examples of the inert solvent include dichloromethane, chloroform, carbon tetrachloride, N,N-dimethylformamide and the like. The reaction is usually carried out at a temperature between 0° C. and 50° C. for 5 minutes to 24 hours.

Starting material, Compound (IId) can be obtained as a commercially available product or according to a known method [e.g. R. C. Larock, Comprehensive Organic Transformations, second edition, John Wiley & Sons Inc. (1999)] or methods similar thereto.

Production Method 2:

Compound (Ia), i.e. Compound (I) in which $R^2$ is —$OR^{16b}$ (wherein $R^{16b}$ represents substituted or unsubstituted lower alkyl in the definition of $R^{16}$) can also be produced according to the following process.

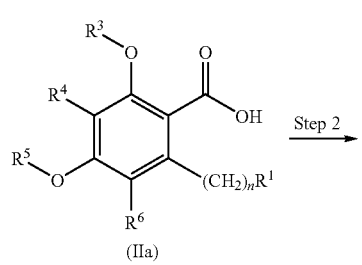

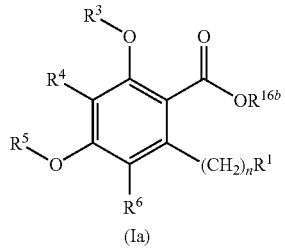

(wherein $R^1$, $R^3$ to $R^6$, $R^{16b}$ and n have the same meanings as defined above, respectively)

Compound (Ia) can be obtained by alkylating reaction of Compound (IIa).

For example, Compound (Ia) can be obtained by reacting Compound (IIa) with 1 to 20 equivalents of corresponding alkylating agent such as, diazomethane, trimethylsilyldiazomethane, and $R^{16b}Y$ (wherein $R^{16b}$ has the same meaning as defined above and Y has the same meaning as the above X) in a solvent. If necessary, 1 to 20 equivalents of a base may be added thereto. In general, the reaction is carried out at a temperature between −20° C. and the boiling point of the solvent for 5 minutes to 24 hours.

Examples of the solvent include halogenated hydrocarbons such as dichloromethane and chloroform; esters such as methyl acetate, ethyl acetate and isobutyl acetate; ethers such as diethylether, tetrahydrofuran and 1,4-dioxane; aromatic hydrocarbons such as benzene and toluene; acetonitrile; N,N-dimethylformamide; N-methylpiperidone; hexane; and mixed solvent thereof. When $R^{16b}$ is methyl, methanol or a mixture of methanol and the above-mentioned solvent can be used as solvents. When $R^{16b}$ is ethyl, ethanol or a mixture of ethanol and the above-mentioned solvent can be used as solvents.

Examples of the base include alkylamines such as triethylamine, diisopropyl ethylamine and N-methylmorpholine; pyridines such as pyridine, lutidine, collidine and 4-dimethylaminopyridine; alkali metal carbonates such as potassium carbonate and sodium hydrogencarbonate; and alkali metal hydroxides such as potassium hydroxide, sodium hydroxide, and lithium hydroxide.

Further, the transformation of the functional groups in Compound (I), the starting materials and the intermediates and the transformation of the functional groups contained in the substituents can be carried out according to a known method [e.g. R. C. Larock, Comprehensive Organic Transformations, second edition, John Wiley & Sons Inc. (1999)] or methods similar thereto.

By appropriately combining the above-described processes and the like, Compound (I) having desired functional groups at desired positions can be obtained.

The intermediates and the desired compounds in the above-described production methods can be isolated and purified by appropriately combining separation and purification methods conventionally used in synthetic organic chemistry, for example, filtration, extraction, washing, drying, concentration, recrystallization, and various kinds of chromatography. The intermediates can also be subjected to the subsequent reactions without purification.

For some of Compound (I) or a prodrug thereof, there may exist stereoisomers such as geometrical isomers and optical isomers, and all possible isomers including them and mixtures thereof can be used for the Hsp90 family protein inhibitors of the present invention.

When it is desired to obtain a salt of Compound (I) or a prodrug thereof, in the case where Compound (I) or a prodrug thereof is produced in the form of the salt, it can be purified as such, and where it is produced in the free form, it can be converted into a salt by dissolving or suspending it in an appropriate solvent and then adding an acid or a base thereto.

Further, Compound (I) or a prodrug thereof and a pharmaceutically acceptable salt of said compound or said prodrug may exist in the form of adducts with water or various solvents, and these adducts can also be used for the Hsp90 family protein inhibitors of the present invention.

Examples of Compound (I) obtained by the present invention are shown in Table 1.

TABLE 1

(I)

| Compd. | $R^1$ | n | $R^2$ | $R^3$ | $R^4$ | $R^5$ | $R^6$ |
|---|---|---|---|---|---|---|---|
| 1 | ![benzyl-OMe] | 1 | ![N-methylanilino] | H | H | H | H |
| 2 | ![benzyl-OMe] | 1 | ![N-methylbenzylamino] | H | H | H | H |
| 3 | ![benzyl-OMe] | 1 | ![N-methylphenethylamino] | H | H | H | H |
| 4 | ![benzyl-OMe] | 1 | OCH$_3$ | H | H | H | Cl |
| 5 | ![benzyl-OMe] | 1 | ![N-methylbenzylamino] | H | H | H | Cl |
| 6 | ![benzyl-OMe] | 1 | ![2-methoxybenzyl-N-methylamino] | H | H | H | Cl |
| 7 | ![benzyl-OMe] | 1 | ![3-methoxybenzyl-N-methylamino] | H | H | H | Cl |
| 8 | ![benzyl-OMe] | 1 | ![4-methoxybenzyl-N-methylamino] | H | H | H | Cl |

TABLE 1-continued (I)

| Compd. | R¹ | n | R² | R³ | R⁴ | R⁵ | R⁶ |
|---|---|---|---|---|---|---|---|
| 9 | benzyl methyl ether (OCH₂-C₆H₅ via OMe-benzyl) | 1 | –NH–CH₂-(2-pyridyl) | H | H | H | Cl |
| 10 | benzyl methyl ether | 1 | OCH₃ | H | H | H | Br |
| 11 | CO₂CH₃ | 1 | N(CH₃)₂ | H | H | H | CH₂CH₃ |
| 12 | CO₂CH₃ | 1 | 1-pyrrolidinyl | H | H | H | CH₂CH₃ |
| 13 | CO₂CH₃ | 1 | –N(CH₃)–CH₂-C₆H₅ with N-CH₃ | H | H | H | CH₂CH₃ |
| 14 | CO₂CH₃ | 1 | 4-morpholinyl | H | H | H | CH₂CH₃ |
| 15 | CO₂CH₃ | 1 | –N(CH₃)–CH₂CH₂CH₃ (with N-CH₃) | H | H | H | CH₂CH₃ |
| 16 | CO₂CH₃ | 1 | –N(CH₃)–CH₂CH₂–OCH₃ | H | H | H | CH₂CH₃ |
| 17 | CO₂CH₃ | 1 | 1-piperidinyl | H | H | H | CH₂CH₃ |
| 18 | CO₂CH₃ | 1 | 4-methylpiperazin-1-yl | H | H | H | CH₂CH₃ |
| 19 | OH | 2 | –NH–CH₂-C₆H₅ | H | H | H | CH₂CH₃ |
| 20 | OCH₂CH₂OCH₃ | 2 | 4-morpholinyl | H | H | H | CH₂CH₃ |

TABLE 1-continued

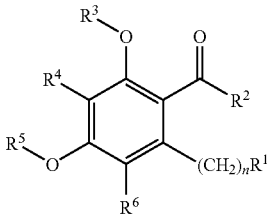

(I)

| Compd. | R¹ | n | R² | R³ | R⁴ | R⁵ | R⁶ |
|---|---|---|---|---|---|---|---|
| 21 | OH | 2 | *N-morpholinylmethyl* | H | H | H | $CH_2CH_3$ |
| 22 | *methoxymethylphenyl* | 1 | $OCH_3$ | H | H | H | H |
| 23 | $CO_2CH_3$ | 1 | $OCH_3$ | H | H | H | $CH_2CH_3$ |

The pharmacological activity of Compound (I) is illustrated below referring to a test example.

TEST EXAMPLE 1

Hsp90 Protein Binding Assay (1) Human N-terminal recombinant Hsp90 protein (region of amino acids 9 to 236) prepared according to the method described in Cell, 1997, Vol. 89, p. 239-250 was diluted to 1 μg/mL with Tris-buffered saline (TBS, pH 7.5) and added to each well of a 96-well ELISA assay plate (Greiner) in an amount of 70 μL/well. The plate was let stand overnight at 4° C. to obtain the solid phase.

(2) The supernatant was removed, and Tris-buffered saline containing 1% bovine serum albumin (BSA) was added in an amount of 350 μL/well for blocking.

(3) After the blocking solution was removed, each resulting solid phase was washed by the addition of Tris-buffered saline containing 0.05% Tween 20 (TBST) in an amount of 500 μL/well. This washing procedure was repeated three times.

(4) A test compound having the highest concentration of 0.1 mmol/L was diluted with TBST to prepare eight/10-fold serial dilutions in separate vials. Each of these test compound solutions was added, in an amount of 10 μL/well, to the assay plate containing TBST (90 μL/well) previously added thereto, and the plate was allowed to stand at 24° C. for 1 hour. In this assay, a positive control using dimethyl sulfoxide (final concentration: 0.1 μL/well) and a negative control using Radicicol (final concentration: 0.29 μmol/L) were subjected to the same procedure as the test compound, and these controls were placed on the same plate as the test compound.

(5) Biotinylated Radicicol represented by Formula (D) (Bioorganic & Medicinal Chemistry, 2002, Vol. 10, p. 3445-3454) was added to give a final concentration of 0.1 μmol/L, and the plate was incubated at 24° C. for further 1 hour for competitive binding reaction to measure the binding activity of the test compound to the immobilized Hsp90 protein.

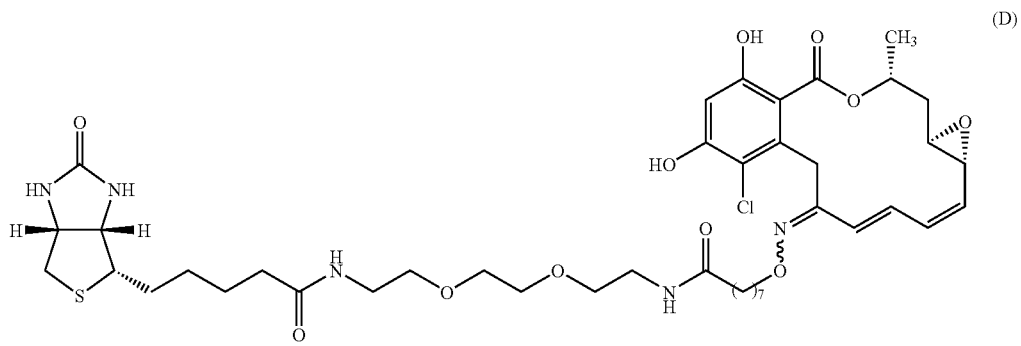

(D)

(6) After the reaction mixture of (5) was removed, each resulting solid phase was washed by the addition of TBST in an amount of 500 μL/well. This washing procedure was repeated three times.

(7) Europium-labeled streptoavidin (Wallac Oy) was diluted, to a final concentration of 0.1 μg/mL with Assay Buffer (Wallac Oy) and added to the wells of the plate in an amount of 100 μL/well. The plate was incubated at room temperature for 1 hour to carry out biotin-avidin binding reaction.

(8) After the reaction mixture of (7) was removed, each resulting solid phase was washed by the addition of TBST in an amount of 500 μL/well. This washing procedure was repeated four times more.

(9) Enhancement solution (Wallac Oy) was added thereto in an amount of 100 μL/well and color developing reaction was carried out at room temperature for 5 minutes, followed by measurement of time-resolved fluorescence (excitation wavelength: 340 nm, measurement wavelength: 615 nm) using Multilabel Counter (ARVO 1420, Wallac Oy).

The binding rate in each well treated the test compound was calculated from the time-resolved fluorescence measured for each well based on the time-resolved fluorescence measured with the positive control taken as 100% binding rate and that with the negative control taken as 0% binding rate.

In the above method, it was revealed that Compounds 2 to 4, 9, 11 to 14, 17 to 19, and 23 inhibited the binding of biotinylated Radicicol to the Hsp90 protein by more than 30% at concentrations below 10 μmol/L and thus have Hsp90 protein-binding activity.

As described above, benzoquinone ansamycin antibiotics such as Geldanamycin and Herbimycin, Radicicol and the like are known as compounds which bind to Hsp90 family proteins (Cell Stress & Chaperones, 1998, Vol. 3, p. 100-108; J. Med. Chem., 1999, Vol. 42, p. 260-266) and these compounds are all reported to bind to Hsp90 family proteins and inhibit the functions of Hsp90 family proteins, thereby exhibiting pharmacological activities such as anti-tumor activity. Further, it is reported that a Geldanamycin derivative (17-AAG; Invest. New Drugs, 1999, No. 17, p. 361-373) and Radicicol derivatives (Cancer Research, 1999, No. 59, p. 2931-2938; Blood, 2000, No. 96, p. 2284-2291; Cancer Chemotherapy and Pharmacology, 2001, No. 48, p. 435-445; WO96/33989; WO98/18780; WO99/55689; WO02/16369) show anti-tumor effect.

Therefore, Compound (I) is considered to be useful as therapeutic agents for diseases associated with Hsp90 family proteins or proteins to which Hsp90 family proteins bind (Hsp90 client proteins) (e.g. anti-tumor agents).

TEST EXAMPLE 2

Growth Inhibition Test on Human Mammary Cancer-Derived KPL-4 Cells

Two thousand cells of human mammary cancer-derived KPL-4 cells were inoculated into each well of a 96-well microplate (manufactured by Nunc Corp.), and using Dulbecco's Modified Eagle's Medium (DMEM) (culture medium) containing 10% fetal calf serum (FCS), preculturing was performed in a 5% carbon dioxide incubator at 37° C. for 24 hours. A dimethyl sulfoxide (DMSO) solution of each test compound prepared in a concentration of 10 mmol/L was diluted with the culture medium step-by-step to a final concentration of 100 μL/well, and the diluted solution was added to each well. The individual wells were further cultured in the 5% carbon dioxide incubator at 37° C. for 72 hours. After completion of the culturing, 20 μL of WST-1 {4-[3-(4-Iodophenyl)-2-(4-nitrophenyl)-2H-5-tetrazolio]-1,3-benzene disulfonate} reagent mixture (manufactured by Roche Diagnostic Corp.) diluted to twice its original amount by culture medium was added to each well, and culturing was performed in the 5% carbon dioxide incubator at 37° C. for 1 hour. Using a microplate spectrophotometer (Model 550; manufactured by Bio-Rad), the absorbance of each well was measured at 450 nm and 655 nm. The cell growth inhibitory activity was expressed as 50% growth inhibitory concentration ($GI_{50}$). The method for calculating the $GI_{50}$ value is as follows. A value obtained by subtracting the absorbance at 655 nm from the absorbance at 450 nm (absorbance difference) was calculated for each well. The absorbance difference obtained for cells not treated with a test compound was designated as 100%, which was compared with the absorbance difference obtained for cells treated with each compound at various test concentrations, and thus the compound concentration at which cell growth was inhibited by 50% was calculated to determine the $GI_{50}$ value.

Results obtained by using the method described above show that Compounds 1 to 3, 9, 10, 14 to 19, and 23 each exhibit, at a $GI_{50}$ value of 50 μmol/L or less, cell growth inhibitory activity against human mammary cancer-derived KPL-4 cells, and these compounds are considered to be useful as antitumor agents.

TEST EXAMPLE 3

Growth Inhibition Test on Human Chronic Myelocytic Leukemia K562 Cells

Fifteen hundred cells of human chronic myelocytic leukemia K562 cells are inoculated into each well of a 96-well microplate (manufactured by Nunc Corp.), and using Rosewell Park Memorial Institute's Medium (RPMI) (manufactured by Nippon Suisan Kaisha, Ltd.) (culture medium) containing 10% FCS, preculturing is performed in a 5% carbon dioxide incubator at 37° C. for 5 hours. A DMSO solution of each test compound prepared in a concentration of 10 mmol/L is diluted with the culture medium step-by-step to a final concentration of 100 μL/well, and the diluted solution is added to each well. The individual wells are further cultured in the 5% carbon dioxide incubator at 37° C. for 72 hours. After completion of the culturing, 20 μL of WST-1 reagent mixture (manufactured by Roche Diagnostic Corp.) diluted to twice its original amount by culture medium is added to each well, and culturing is performed in the 5% carbon dioxide incubator at 37° C. for 2 hours. Using a microplate spectrophotometer (Model 550; manufactured by Bio-Rad), the absorbance of each well is measured at 450 nm and 655 nm. The cell growth inhibitory activity is expressed as 50% growth inhibitory concentration ($GI_{50}$) in a similar manner to Test Example 2.

Results obtained by using the method described above show that Compound (I) exhibits cell growth inhibitory activity against human chronic myelocytic leukemia K562 cells, and these compounds are considered to be useful as antitumor agents.

Although Compound (I), a prodrug thereof, or a pharmaceutically acceptable salt of said Compound (I) or said prodrug can be administered alone, as such, it is generally preferred to offer them in the form of various pharmaceutical preparations. Such pharmaceutical preparations are to be used in animals and humans.

The pharmaceutical preparations of the present invention can comprise Compound (I) or a prodrug thereof, or a pharmaceutical salt of said Compound (I) or said prodrug as the active ingredient alone or in combination with any other active ingredients for the therapy. These pharmaceutical preparations may be produced by any methods well known in the technical field of pharmaceutics by mixing the active ingredient with one or more pharmaceutically acceptable carriers.

It is desirable to select a route of administration that is most effective for the therapy, examples thereof being oral administration or parenteral administration such as intravenous.

Examples of the dosage form include tablets and injections.

Preparations suitable for oral administration such as tablets can be produced using, for example, excipients (e.g., lactose and mannitol), disintegrators (e.g., starch), lubricants (e.g., magnesium stearate), binders (e.g., hydroxypropyl cellulose), surfactants (e.g., fatty acid esters) and plasticizers (e.g., glycerin).

Preparations suitable for parenteral administration preferably comprise a sterilized aqueous preparation containing an active compound which is isotonic to the recipient's blood. In the case of an injection, for example, a solution for injection is prepared using a carrier comprising a saline solution, a glucose solution, or a mixture of a saline solution and a glucose solution. The parenteral preparations may also comprise one or more auxiliary components selected from the excipients, disintegrators, lubricants, binders, surfactants and plasticizers described in the above description of oral preparations and diluents, antiseptics, flavors, etc.

The dose and the administration schedule of Compound (I) or a prodrug thereof, or a pharmaceutical salt of said Compound (I) or said prodrug will vary-depending upon the administration route, the age and body weight of a patient, and the nature and degree of severeness of the symptom to be treated. In general, in the case of oral administration, the active ingredient is administered in a dose of 0.01 mg to 1 g, preferably 0.05 to 50 mg, per adult once to several times per day. In the case of parenteral administration such as intravenous administration, the active ingredient is administered in a dose of 0.001 to 500 mg, preferably 0.01 to 100 mg, per adult once to several times per day. However, the dose and the administration schedule may vary depending upon various conditions as given above.

Certain embodiments of the present invention are illustrated in the following examples and reference examples.

Example 1

2-(Benzyloxymethyl)-4,6-dihydroxy-N-phenylbenzamide (Compound 1)

(Step 1)

2-(Benzyloxymethyl)-4,6-bis(methoxymethoxy)benzoic acid (35 mg, 0.0096 mmol) obtained in Step 6 of Example 22 was dissolved in tetrahydrofuran (4 mL) and dichloromethane (1 mL), and aniline (0.030 mL, 0.33 mmol), 1-hydroxybenzotriazole monohydrate (56 mg, 0.37 mmol) and 1-[3-(dimethylamino)propyl]-3-ethylcarbodiimide hydrochloride (0.13 g, 0.68 mmol) were added to the obtained solution followed by stirring at a room temperature for 20 hours. The reaction mixture was concentrated under reduced pressure and the obtained residue was purified by preparative thin-layer chromatography (chloroform/methanol=100/1) to obtain 2-(benzyloxymethyl)-4,6-bis(methoxymethoxy)-N-phenylbenzamide (20 mg, 49%).

$^1$H-NMR (270 MHz, CDCl$_3$) δ (ppm): 3.47 (s, 3H), 3.48 (s, 3H), 4.57 (s, 2H), 4.68 (s, 2H), 5.19 (s, 2H), 5.20 (s, 2H), 6.82 (d, J=2.6 Hz, 1H), 6.91 (d, J=2.6 Hz, 1H), 7.00-7.20 (m, 1H), 7.20-7.45 (m, 7H), 7.50-7.60 (m, 2H).

(Step 2)

The above-obtained 2-(benzyloxymethyl)-4,6-bis(methoxymethoxy)-N-phenylbenzamide (18 mg, 0.043 mmol) was dissolved in ethanol (4 mL) and the obtained solution was added with concentrated hydrochloric acid (0.10 mL) followed by stirring at 60° C. for 1 hour. The reaction mixture was concentrated under reduced pressure and the residue was purified by preparative thin-layer chromatography (chloroform/methanol=20/1) to obtain Compound 1 (14 mg, 92%).

$^1$H-NMR (270 MHz, CDCl$_3$) δ(ppm): 4.66 (s, 2H), 4.68 (s, 2H), 5.27 (brs, 1H), 6.33 (d, J=2.6 Hz, 1H), 6.47 (d, J=2.6 Hz, 1H), 7.00-7.50 (m, 10H), 10.52 (brs, 1H), 12.34 (s, 1H); APCI-MS (m/z): 348 (M−H)$^-$.

Example 2

N-benzyl-2-(benzyloxymethyl)-4,6-dihydroxybenzamide (Compound 2)

(Step 1)

In a similar manner to Step 1 of Example 1, N-benzyl-2-(benzyloxymethyl)-4,6-bis(methoxymethoxy)benzamide (26 mg, 60%) was obtained from 2-(benzyloxymethyl)-4,6-bis(methoxymethoxy)benzoic acid (35 mg, 0.096 mmol) obtained in Step 6 of Example 22, using tetrahydrofuran (4 mL), dichloromethane (1 mL), benzylamine (0.032 mL, 0.29 mmol), 1-hydroxybenzotriazole monohydrate (60 mg, 0.39 mmol) and 1-[3-(dimethylamino)propyl]-3-ethylcarbodiimide hydrochloride (0.11 g, 0.57 mmol).

$^1$H-NMR (270 MHz, CDCl$_3$) δ(ppm): 3.41 (s, 3H), 3.46 (s, 3H), 4.51 (s, 2H), 4.59 (d, J=5.8 Hz, 2H), 4.62 (s, 2H), 5.14 (s, 2H), 5.16 (s, 2H), 6.39 (brt, J=5.8 Hz, 1H), 6.76 (d, J=2.1 Hz, 1H), 6.88 (d, J=2.1 Hz, 1H), 7.20-7.50 (m, 10H).

(Step 2)

In a similar manner to Step 2 of Example 1, Compound 2 (19 mg, 100%) was obtained from N-benzyl-2-(benzyloxymethyl)-4,6-bis(methoxymethoxy)benzamide (24 mg, 0.053 mmol), using ethanol (4 mL) and concentrated hydrochloric acid (0.10 mL).

$^1$H-NMR (270 MHz, CDCl$_3$) δ(ppm): 4.35 (s, 2H), 4.49 (s, 2H), 4.54 (d, J=5.4 Hz, 2H), 5.19 (brs, 1H), 6.26 (d, J=2.6 Hz, 1H), 6.43 (d, J=2.6 Hz, 1H), 7.00-7.15 (m, 2H), 7.20-7.50 (m, 8H), 8.97 (brs, 1H), 12.63 (brs, 1H); APCI-MS (m/z): 362 (M−H)$^-$.

Example 3

2-(Benzyloxymethyl)-4,6-dihydroxy-N-phenethylbenzamide (Compound 3)

(Step 1)

In a similar manner to Step 1 of Example 1, 2-(benzyloxymethyl)-4,6-bis(methoxymethoxy)-N-phenethylbenzamide (27 mg, 69%) was obtained from 2-(benzyloxymethyl)-4,6-bis(methoxymethoxy)benzoic acid (32 mg, 0.88 mmol) obtained in Step 6 of Example 22, using tetrahydrofuran (4 mL), dichloromethane (1 mL), phenethylamine (0.030 mL, 0.24 mmol), 1-hydroxybenzotriazole monohydrate (68 mg, 0.44 mmol) and 1-[3-(dimethylamino)propyl]-3-ethylcarbodiimide hydrochloride (0.11 g, 0.57 mmol).

$^1$H-NMR (270 MHz, CDCl$_3$) δ(ppm): 2.87 (t, J=6.8 Hz, 2H), 3.38 (s, 3H), 3.45 (s, 3H), 3.69 (dt, J=5.9, 6.8 Hz, 2H), 4.54 (s, 2H), 4.59 (s, 2H), 5.05 (s, 2H), 5.15 (s, 2H), 6.12 (brt, J=5.9 Hz, 1H), 6.74 (d, J=2.3 Hz, 1H), 6.89 (d, J=2.3 Hz, 1H), 7.15-7.40 (m, 10H).

(Step 2)

In a similar manner to Step 2 of Example 1, Compound 3 (18 mg, 87%) was obtained from 2-(benzyloxymethyl)-4,6-bis(methoxymethoxy)-N-phenethylbenzamide (25 mg, 0.055 mmol), using ethanol (4 mL) and concentrated hydrochloric acid (0.10 mL).

$^1$H-NMR (270 MHz, CDCl$_3$) δ(ppm): 2.85 (t, J=7.0 Hz, 1H), 3.62 (dt, J=5.6, 7.0 Hz, 2H), 4.31 (s, 2H), 4.33 (s, 2H), 5.20 (brs, 1H), 6.21 (d, J=2.5 Hz, 1H), 6.42 (d, J=2.5 Hz, 1H), 7.10-7.50 (m, 10H), 8.69 (brs, 1H), 12.74 (brs, 1H); APCI-MS (m/z): 378 (M+H)$^+$.

Example 4

2-(Benzyloxymethyl)-3-chloro-4,6-dihydroxybenzoic acid methyl ester (Compound 4)

(Step 1)

2-(Benzyloxymethyl)-4,6-bis(methoxymethoxy)benzaldehyde (0.12 g, 0.33 mmol) obtained in Step 5 of Example 22 was dissolved in tetrahydrofuran (10 mL), and sodium chlorite (0.32 g, 3.6 mmol), amidosulfonic acid (0.69 g, 7.1 mmol), and distilled water (5 mL) were added to the obtained solution followed by stirring at a room temperature for 3 hours. The reaction mixture was added with water and was extracted with chloroform 3 times. The organic layers were combined and sequentially washed with saturated aqueous sodium thiosulfate solution and saturated brine, and dried over anhydrous sodium sulfate. The solvent was evaporated under reduced pressure to obtain 2-(benzyloxymethyl)-3-chloro-4,6-bis(methoxymethoxy)benzoic acid (0.17 g, 100%).

$^1$H-NMR (270 MHz, CDCl$_3$) δ(ppm): 3.30 (brs, 1H), 3.45 (s, 3H), 3.51 (s, 3H), 4.54 (s, 2H), 4.81 (s, 2H), 5.15 (s, 2H), 5.25 (s, 2H), 7.02 (s, 1H), 7.20-7.40 (m, 5H).

(Step 2)

2-(Benzyloxymethyl)-3-chloro-4,6-bis(methoxymethoxy)benzoic acid (25 mg, 0.063 mmol) obtained above was dissolved in methanol (2 mL), and hexane solution of 2.0 mol/L trimethylsilyldiazomethane (0.30 mL, 0.60 mmol) was added thereto followed by stirring at a room temperature for 1 hour. After adding acetic acid (0.050 mL) to the reaction mixture, the solvent was evaporated under reduced pressure. The residue was purified by preparative thin-layer chromatography (chloroform/methanol=100/1) to obtain 2-(benzyloxymethyl)-3-chloro-4,6-bis(methoxymethoxy)benzoic acid methyl ester (17 mg, 65%).

$^1$H-NMR (270 MHz, CDCl$_3$) δ(ppm): 3.47 (s, 3H), 3.51 (s, 3H), 3.72 (s, 3H), 4.51 (s, 2H), 4.75 (s, 2H), 5.15 (s, 2H), 5.25 (s, 2H), 7.00 (s, 1H), 7.20-7.40 (m, 5H).

(Step 3)

In a similar manner to Step 2 of Example 1, Compound 4 (10 mg, 77%) was obtained from 2-(benzyloxymethyl)-3-chloro-4,6-bis(methoxymethoxy)benzoic acid methyl ester (16 mg, 0.038 mmol) obtained above, using ethanol (4 mL) and concentrated hydrochloric acid (0.10 mL).

$^1$H-NMR (270 MHz, CDCl$_3$) δ(ppm): 3.84 (s, 3H), 4.56 (s, 2H), 4.93 (s, 2H), 6.08 (brs, 1H), 6.64 (s, 1H), 7.20-7.40 (m, 5H), 11.01 (brs, 1H); APCI-MS (m/z): 321 (M−H)$^-$.

Example 5

N-benzyl-2-(benzyloxymethyl)-3-chloro-4,6-dihydroxybenzamide (Compound 5)

(Step 1)

In a similar manner to Step 1 of Example 1, N-benzyl-2-(benzyloxymethyl)-3-chloro-4,6-bis(methoxymethoxy)benzamide (5.9 mg, 1.4%) was obtained from 2-(benzyloxymethyl)-3-chloro-4,6-bis(methoxymethoxy)benzoic acid (37 mg, 0.093 mmol) obtained in Step 1 of Example 4, using tetrahydrofuran (4 mL), dichloromethane (1 mL), benzylamine (0.033 mL, 0.30 mmol), 1-hydroxybenzotriazole monohydrate (62 mg, 0.40 mmol) and 1-[3-(dimethylamino)propyl]-3-ethylcarbodiimide hydrochloride (94 mg, 0.49 mmol).

$^1$H-NMR (270 MHz, CDCl$_3$) δ(ppm): 3.49 (s, 3H), 4.39 (s, 2H), 4.53 (d, J=5.3 Hz, 2H), 4.77 (s, 2H), 5.25 (s, 2H), 6.82 (s, 1H), 7.00-7.40 (m, 10H), 8.64 (brs, 1H), 11.93 (brs, 1H).

(Step 2)

In a similar manner to Step 2 of Example 1, Compound 5 (4.1 mg, 79%) was obtained from N-benzyl-2-(benzyloxymethyl)-3-chloro-4,6-bis(methoxymethoxy)benzamide (5.9 mg, 0.013 mmol) obtained above, using ethanol (4 mL) and concentrated hydrochloric acid (0.10 mL).

$^1$H-NMR (270 MHz, CDCl$_3$) δ(ppm): 4.36 (s, 2H), 4.53 (d, J=5.3 Hz, 2H), 4.70 (s, 2H), 5.89 (brs, 1H), 6.67 (s, 1H), 7.00-7.15 (m, 2H), 7.20-7.40 (m, 8H), 8.54 (brs, 1H), 11.85 (brs, 1H); APCI-MS (m/z): 398 (M+H)$^+$.

Example 6

2-(Benzyloxymethyl)-3-chloro-4,6-dihydroxy-N-(2-methoxybenzyl)benzamide (Compound 6)

(Step 1)

In a similar manner to Step 1 of Example 1, 2-(benzyloxymethyl)-3-chloro-N-(2-methoxybenzyl)-4,6-bis(methoxymethoxy)benzamide (9.5 mg, 23%) was obtained using 2-(benzyloxymethyl)-3-chloro-4,6-bis(methoxymethoxy)benzoic acid (34 mg, 0.087 mmol), obtained in Step 1 of Example 4, tetrahydrofuran (4 mL), dichloromethane (1 mL), 2-methoxybenzylamine (0.039 mL, 0.30 mmol), 1-hydroxybenzotriazole monohydrate (59 mg, 0.39 mmol) and 1-[3-(dimethylamino)propyl]-3-ethylcarbodiimide hydrochloride (0.11 g, 0.57 mmol).

$^1$H-NMR (270 MHz, CDCl$_3$) δ(ppm): 3.49 (s, 3H), 3.70 (s, 3H), 4.39 (s, 2H), 4.56 (d, J=4.9 Hz, 2H), 4.73 (s, 2H), 5.24 (s, 2H), 6.80 (s, 1H), 6.75-6.95 (m, 2H), 7.10-7.20 (m, 2H), 7.20-7.40 (m, 5H), 8.48 (brs, 1H), 11.93 (brs, 1H).

(Step 2)

In a similar manner to Step 2 of Example 1, Compound 6 (5.8 mg, 68%) was obtained from 2-(benzyloxymethyl)-3-chloro-N-(2-methoxybenzyl)-4,6-bis(methoxymethoxy)benzamide (9.5 mg, 0.02 mmol) obtained above, using ethanol (4 mL) and concentrated hydrochloric acid (0.10 mL).

$^1$H-NMR (270 MHz, CDCl$_3$) δ(ppm): 3.70 (s, 3H), 4.36 (s, 2H), 4.56 (d, J=5.3 Hz, 2H), 4.66 (s, 2H), 5.89 (brs, 1H), 6.65 (s, 1H), 6.84 (brd, J=8.4 Hz, 1H), 6.91 (ddd, J=1.0, 7.4, 7.4

Hz, 1H), 7.10-7.20 (m, 2H), 7.20-7.40 (m, 5H), 8.38 (brs, 1H), 11.85 (brs, 1H); APCI-MS (m/z): 426 (M−H)⁻.

Example 7

2-(Benzyloxymethyl)-3-chloro-4,6-dihydroxy-N-(3-methoxybenzyl)benzamide (Compound 7)

(Step 1)

In a similar manner to Step 1 of Example 1, 2-(benzyloxymethyl)-3-chloro-N-(3-methoxybenzyl)-4,6-bis(methoxymethoxy)benzamide (9.0 mg, 23%) was obtained from 2-(benzyloxymethyl)-3-chloro-4,6-bis(methoxymethoxy)benzoic acid (33 mg, 0.084 mmol) obtained in Step 1 of Example 4, using tetrahydrofuran (4 mL), dichloromethane (1 mL), 3-methoxybenzylamine (0.038 mL, 0.30 mmol), 1-hydroxybenzotriazole monohydrate (68 mg, 0.44 mmol) and 1-[3-(dimethylamino)propyl]-3-ethylcarbodiimide hydrochloride (98 mg, 0.51 mmol).

$^1$H-NMR (270 MHz, CDCl$_3$) δ(ppm): 3.49 (s, 3H), 3.76 (s, 3H), 4.41 (s, 2H), 4.50 (d, J=5.3 Hz, 2H), 4.77 (s, 2H), 5.25 (s, 2H), 6.82 (s, 1H), 6.70-6.90 (m, 3H), 7.00-7.40 (m, 6H), 8.63 (brt, J=5.3 Hz, 1H), 11.91 (brs, 1H).

(Step 2)

In a similar manner to Step 2 of Example 1, Compound 7 (5.1 mg, 63%) was obtained from 2-(benzyloxymethyl)-3-chloro-N-(3-methoxybenzyl)-4,6-bis(methoxymethoxy)benzamide (9.0 mg, 0.019 mmol) obtained above, using ethanol (4 mL) and concentrated hydrochloric acid (0.10 mL).

$^1$H-NMR (270 MHz, CDCl$_3$) δ(ppm): 3.76 (s, 3H), 4.38 (s, 2H), 4.50 (d, J=4.5 Hz, 2H), 4.70 (s, 2H), 5.92 (brs, 1H), 6.67 (s, 1H), 6.80-6.90 (m, 3H), 7.00-7.20 (m, 2H), 7.20-7.40 (m, 4H), 8.52 (brt, J=5.3 Hz, 1H), 11.83 (brs, 1H); APCI-MS (m/z): 426 (M−H)⁻.

Example 8

2-(Benzyloxymethyl)-3-chloro-4,6-dihydroxy-N-(4-methoxybenzyl)benzamide (Compound 8)

(Step 1)

In a similar manner to Step 1 of Example 1, 2-(benzyloxymethyl)-3-chloro-N-(4-methoxybenzyl)-4,6-bis(methoxymethoxy)benzamide (6.2 mg, 16%) was obtained from 2-(benzyloxymethyl)-3-chloro-4,6-bis(methoxymethoxy)benzoic acid (33 mg, 0.083 mmol) obtained in Step 1 of Example 4, using tetrahydrofuran (4 mL), dichloromethane (1 mL), 4-methoxybenzylamine (0.039 mL, 0.30 mmol), 1-hydroxybenzotriazole monohydrate (65 mg, 0.42 mmol) and 1-[3-(dimethylamino)propyl]-3-ethylcarbodiimide hydrochloride (0.11 g, 0.57 mmol).

$^1$H-NMR (270 MHz, CDCl$_3$) δ(ppm): 3.49 (s, 3H), 3.79 (s, 3H), 4.40 (s, 2H), 4.47 (d, J=5.3 Hz, 2H), 4.76 (s, 2H), 5.25 (s, 2H), 6.75-6.85 (m, 3H), 7.00-7.40 (m, 7H), 8.57 (brt, J=5.3 Hz, 1H), 11.95 (brs, 1H).

(Step 2)

In a similar manner to Step 2 of Example 1, Compound 8 (3.7 mg, 67%) was obtained from 2-(benzyloxymethyl)-3-chloro-N-(4-methoxybenzyl)-4,6-bis(methoxymethoxy)benzamide (6.2 mg, 0.013 mmol) obtained above, using ethanol (4 mL) and concentrated hydrochloric acid (0.10 mL).

$^1$H-NMR (270 MHz, CDCl$_3$) δ(ppm): 3.79 (s, 3H), 4.37 (s, 2H), 4.47 (d, J=5.1 Hz, 2H), 4.69 (s, 2H), 5.90 (brs, 1H), 6.66 (s, 1H), 6.82 (d, J=8.7 Hz, 2H), 7.00-7.40 (m, 7H), 8.46 (brt, J=5.1 Hz, 1H), 11.88 (brs, 1H); APCI-MS (m/z): 426 (M−H)—.

Example 9

2-(Benzyloxymethyl)-3-chloro-4,6-dihydroxy-N-(pyridin-2-ylmethyl)benzamide (Compound 9)

(Step 1)

In a similar manner to Step 1 of Example 1, 2-(benzyloxymethyl)-3-chloro-4,6-bis(methoxymethoxy)-N-(pyridin-2-ylmethyl)benzamide (21.0 mg, 33%) was obtained from 2-(benzyloxymethyl)-3-chloro-4,6-bis(methoxymethoxy)benzoic acid (51 mg, 0.13 mmol) obtained in Step 1 of Example 4, using tetrahydrofuran (4 mL), dichloromethane (1 mL), 2-pyridylmethylamine (0.040 mL, 0.39 mmol), 1-hydroxybenzotriazole monohydrate (92 mg, 0.60 mmol) and 1-[3-(dimethylamino)propyl]-3-ethylcarbodiimide hydrochloride (0.13 g, 0.68 mmol).

$^1$H-NMR (270 MHz, CDCl$_3$) δ(ppm): 3.42 (s, 3H), 3.51 (s, 3H), 4.50 (s, 2H), 4.67 (s, 2H), 4.70 (d, J=4.9 Hz, 2H), 5.14 (s, 2H), 5.25 (s, 2H), 7.03 (s, 1H), 7.15-7.40 (m, 8H), 7.60-7.67 (m, 1H), 8.40-8.52 (m, 1H).

(Step 2)

In a similar manner to Step 2 of Example 1, Compound 9 (8.9 mg, 52%) was obtained from 2-(benzyloxymethyl)-3-chloro-4,6-bis(methoxymethoxy)-N-(pyridin-2-ylmethyl)benzamide (21.0 mg, 0.043 mmol) obtained above, using ethanol (4 mL) and concentrated hydrochloric acid (0.10 mL).

$^1$H-NMR (270 MHz, CDCl$_3$) δ(ppm): 3.45-3.52 (m, 1H), 4.65 (s, 2H), 4.71 (d, J=5.3 Hz, 2H), 4.80 (s, 2H), 5.95 (brs, 1H), 6.65 (s, 1H), 7.20-7.32 (m, 8H), 7.60-7.65 (m, 1H), 8.40-8.45 (m, 1H); APCI-MS (m/z): 399 (M+H)⁺.

Example 10

2-(Benzyloxymethyl)-3-bromo-4,6-dihydroxybenzoic acid methyl ester (Compound 10)

(Step 1)

2-(Benzyloxymethyl)-4,6-bis(methoxymethoxy)benzoic acid (60 mg, 0.17 mmol) obtained in Step 6 of Example 22 was dissolved in N,N-dimethylformamide (10 mL), and N-bromosuccinimide (62 mg, 0.35 mmol) was added thereto followed by stirring at a room temperature for 2 hours. The reaction mixture was added with water and extracted with chloroform 3 times. The organic layers were combined and sequentially washed with saturated aqueous sodium thiosulfate solution and saturated brine, and dried over anhydrous sodium sulfate. The solvent was evaporated under reduced pressure and the obtained residue was purified by preparative thin-layer chromatography (chloroform/methanol=20/1) to obtain 2-(benzyloxymethyl)-3-bromo-4,6-bis(methoxymethoxy)benzoic acid (16 mg, 22%).

$^1$H-NMR (270 MHz, CDCl$_3$) δ(ppm): 3.41 (s, 3H), 3.50 (s, 3H), 4.51 (s, 2H), 4.70 (brs, 1H), 4.80 (s, 2H), 5.11 (s, 2H), 5.23 (s, 2H), 6.96 (s, 1H), 7.20-7.35 (m, 5H).

(Step 2)

The above-obtained 2-(benzyloxymethyl)-3-bromo-4,6-bis(methoxymethoxy)benzoic acid (16 mg, 0.036 mmol) was dissolved in methanol (2 mL) and the obtained mixture was further added with 2.0 mol/L trimethylsilyldiazomethane-hexane solution (0.30 mL, 0.60 mmol) followed by stirring at a room temperature for 1 hour. After adding acetic acid (0.050 mL) to the reaction mixture, the solvent was evaporated under reduced pressure. The obtained residue was dissolved in ethanol (4 mL) and the obtained solution was added with concentrated hydrochloric acid (0.10 mL) followed by stirring at 60° C. for 1 hour. The reaction mixture was concentrated under reduced pressure and the obtained residue was purified by preparative thin-layer chromatography (chloroform/methanol=20/1) to obtain Compound 10 (11 mg, 82%).

$^1$H-NMR (270 MHz, CDCl$_3$) δ(ppm): 3.84 (s, 3H), 4.56 (s, 2H), 4.94 (s, 2H), 6.13 (brs, 1H), 6.66 (s, 1H), 7.20-7.40 (m, 5H), 10.94 (brs, 1H); APCI-MS (m/z): 365, 367 (M−H)$^−$.

Example 11

[2-(N,N-dimethylcarbamoyl)-6-ethyl-3,5-dihydroxyphenyl]acetic acid methyl ester (Compound 11)

(Step 1)

Compound 23 (2.0 g, 7.5 mmol) obtained in Reference Example 1 was dissolved in acetone (50 mL), and potassium carbonate (5.0 g, 36 mmol) and chloromethyl methyl ether (2.5 mL, 33 mmol) were added to the obtained solution followed by stirring at 60° C. for 4 hours. The reaction mixture was added with water and extracted with chloroform 3 times. The organic layers were combined and washed with saturated brine and dried over anhydrous sodium sulfate. The solvent was evaporated under reduced pressure and the obtained residue was purified by silica gel column chromatography (hexane/ethyl acetate=9/1) to obtain 3-ethyl-2-(methoxycarbonylmethyl)-4,6-bis(methoxymethoxy)benzoic acid methyl ester (1.6 g, 61%).

$^1$H-NMR (270 MHz, CDCl$_3$) δ(ppm): 1.07 (t, J=7.5 Hz, 3H), 2.64 (q, J=7.5 Hz, 2H), 3.47 (s, 6H), 3.68 (s, 3H), 3.70 (s, 2H), 3.86 (s, 3H), 5.14 (s, 2H), 5.20 (s, 2H), 6.88 (s, 1H).

(Step 2)

The above-obtained 3-ethyl-2-(methoxycarbonylmethyl)-4,6-bis(methoxymethoxy)benzoic acid methyl ester (1.1 g, 3.0 mmol) was dissolved in methanol (3 mL) and the obtained solution was added with 4.0 mol/L aqueous lithium hydroxide solution (15 mL, 60 mmol) followed by stirring at 60° C. for 30 hours. The reaction mixture was added with water and 6.0 mol/L hydrochloric acid and the pH value was adjusted to 3. Then, the mixture was extracted with ethyl acetate 3 times. The organic layers were combined and dried over anhydrous sodium sulfate. Then, the solvent was evaporated under reduced pressure to obtain 2-(carboxymethyl)-3-ethyl-4,6-bis(methoxymethoxy)benzoic acid (0.91 g, 94%).

$^1$H-NMR (270 MHz, CDCl$_3$) δ(ppm): 1.09 (t, J=7.5 Hz, 3H), 2.77 (q, J=7.5 Hz, 2H), 3.49 (s, 3H), 3.52 (s, 3H), 3.95 (s, 2H), 5.24 (s, 2H), 5.26 (s, 2H), 6.96 (s, 1H).

(Step 3)

The above-obtained 2-(carboxymethyl)-3-ethyl-4,6-bis(methoxymethoxy)benzoic acid (0.38 g, 1.2 mmol) was dissolved in toluene (20 mL) and the obtained solution was added with acetic anhydride (0.20 mL, 2.1 mmol), followed by stirring at 100° C. for 4 hours. The reaction mixture was added with water and then extracted with diethylether 3 times. The organic layers were combined, washed with saturated brine and dried over anhydrous sodium sulfate. Then, the solvent was evaporated under reduced pressure and the obtained residue was dissolved in methanol (20 mL). The obtained solution was added with sodium methoxide (0.22 g, 4.2 mmol) and stirred at a room temperature for 7 hours. After adding water, the reaction mixture was extracted with ethyl acetate 3 times. The organic layers were combined, washed with saturated brine and dried over anhydrous sodium sulfate. Then, the solvent was evaporated under reduced pressure to obtain 3-ethyl-2-(methoxycarbonylmethyl)-4,6-bis(methoxymethoxy)benzoic acid (0.52 g, 100%).

$^1$H-NMR (270 MHz, CDCl$_3$) δ(ppm): 1.07 (t, J=7.5 Hz, 3H), 2.65 (q, J=7.5 Hz, 2H), 3.49 (s, 3H), 3.52 (s, 3H), 3.72 (s, 3H), 3.96 (s, 2H), 5.24 (s, 2H), 5.26 (s, 2H), 6.96 (s, 1H).

(Step 4)

In a similar manner to Step 1 of Example 1, [2-(N,N-dimethylcarbamoyl)-6-ethyl-3,5-bis(methoxymethoxy)phenyl]acetic acid methyl ester (71 mg, 84%) was obtained from 3-ethyl-2-(methoxycarbonylmethyl)-4,6-bis(methoxymethoxy)benzoic acid (79 mg, 0.23 mmol) obtained above, using tetrahydrofuran (4 mL), dichloromethane (1 mL), 50% aqueous dimethylamine solution (0.063 mL, 0.70 mmol), 1-hydroxybenzotriazole monohydrate (0.15 g, 0.98 mmol) and 1-[3-(dimethylamino)propyl]-3-ethylcarbodiimide hydrochloride (0.27 g, 1.4 mmol).

$^1$H-NMR (270 MHz, CDCl$_3$) δ(ppm): 1.06 (t, J=7.4 Hz, 3H), 2.40-2.75 (m, 2H), 2.86 (s, 3H), 3.10 (s, 3H), 3.45 (s, 3H), 3.48 (s, 3H), 3.67 (s, 3H), 5.12 (d, J=9.2 Hz, 1H), 5.14 (d, J=9.2 Hz, 1H), 5.19 (s, 2H), 6.87 (s, 1H).

(Step 5)

In a similar manner to Step 2 of Example 1, Compound 11 (55 mg, 100%) was obtained from [2-(N,N-dimethylcarbamoyl)-6-ethyl-3,5-bis(methoxymethoxy)phenyl]acetic acid methyl ester (69 mg, 0.187 mmol) obtained above, using methanol (4 mL) and concentrated hydrochloric acid (0.10 mL).

$^1$H-NMR (270 MHz, CDCl$_3$) δ(ppm): 1.04 (t, J=7.5 Hz, 3H), 2.35-2.62 (m, 2H), 3.01 (s, 6H), 3.50 (brs, 2H), 3.75 (s, 3H), 5.89 (s, 1H), 6.78 (brs, 1H), 7.54 (brs, 1H); APCI-MS (m/z): 282 (M+H)$^+$.

Example 12

[2-Ethyl-3,5-dihydroxy-6-(pyrrolidin-1-ylcarbonyl)phenyl]acetic acid methyl ester (Compound 12)

(Step 1)

In a similar manner to Step 1 of Example 1, [2-ethyl-3,5-bis(methoxymethoxy)-6-(pyrrolidin-1-ylcarbonyl)phenyl]acetic acid methyl ester (70 mg, 77%) was obtained from 3-ethyl-2-(methoxycarbonylmethyl)-4,6-bis(methoxymethoxy)benzoic acid (79 mg, 0.23 mmol) obtained in Step 3 of Example 11, using tetrahydrofuran (4 mL), dichloromethane (1 mL), pyrrolidine (0.058 mL, 0.70 mmol), 1-hydroxybenzotriazole monohydrate (0.15 g, 0.98 mmol) and 1-[3-(dimethylamino)propyl]-3-ethylcarbodiimide hydrochloride (0.27 g, 1.4 mmol).

$^1$H-NMR (270 MHz, CDCl$_3$) δ(ppm): 1.06 (t, J=7.4 Hz, 3H), 1.70-2.00 (m, 4H), 2.45-2.75 (m, 2H), 3.20-3.68 (m, 6H), 3.46 (s, 3H), 3.48 (s, 3H), 3.66 (s, 3H), 5.12 (d, J=7.6 Hz, 1H), 5.14 (d, J=7.6 Hz, 1H), 5.19 (s, 2H), 6.87 (s, 1H).

(Step 2)

In a similar manner to Step 2 of Example 1, Compound 12 (56 mg, 100%) was obtained from [2-ethyl-3,5-bis(methoxymethoxy)-6-(pyrrolidin-1-ylcarbonyl)phenyl]acetic acid methyl ester (70 mg, 0.18 mmol) obtained above, using methanol (4 mL) and concentrated hydrochloric acid (0.10 mL).

$^1$H-NMR (270 MHz, CDCl$_3$) δ(ppm): 1.03 (t, J=7.5 Hz, 3H), 1.80-2.00 (m, 4H), 2.20-2.70 (m, 2H), 3.20-3.80 (m, 6H), 3.73 (s, 3H), 5.92 (s, 1H), 7.06 (brs, 1H), 7.78 (brs, 1H); APCI-MS (m/z): 308 (M+H)$^+$.

Example 13

[2-(N-benzyl-N-methylcarbamoyl)-6-ethyl-3,5-dihydroxyphenyl]acetic acid methyl ester (Compound 13)

(Step 1)

In a similar manner to Step 1 of Example 1, [2-(N-benzyl-N-methylcarbamoyl)-6-ethyl-3,5-bis(methoxymethoxy)phenyl]acetic acid methyl ester (61 mg, 60%) was obtained from 3-ethyl-2-(methoxycarbonylmethyl)-4,6-bis(methoxymethoxy)benzoic acid (79 mg, 0.23 mmol) obtained in Step 3 of Example 11, using tetrahydrofuran (4 mL), dichloromethane (1 mL), N-methylbenzylamine (0.090 mL, 0.70 mmol), 1-hydroxybenzotriazole monohydrate (0.15 g, 0.98 mmol) and 1-[3-(dimethylamino)propyl]-3-ethylcarbodiimide hydrochloride (0.27 g, 1.4 mmol).

$^1$H-NMR (270 MHz, CDCl$_3$) δ(ppm): 1.06 (t, J=7.4 Hz, 3H), 2.55-2.75 (m, 2H), 2.76 (s, 3H), 3.42 (s, 3H), 3.48 (s, 3H), 3.57 (s, 3H), 3.67 (d, J=17.2 Hz, 1H), 3.88 (d, J=17.2 Hz, 1H), 4.67 (d, J=14.6 Hz, 1H), 4.88 (d, J=14.6 Hz, 1H), 5.12 (d, J=8.6 Hz, 1H), 5.15 (d, J=8.6 Hz, 1H), 5.19 (s, 2H), 6.86 (s, 1H), 7.20-7.40 (m, 5H).

(Step 2)

In a similar manner to Step 2 of Example 1, Compound 13 (48 mg, 99%) was obtained from [2-(N-benzyl-N-methylcarbamoyl)-6-ethyl-3,5-bis(methoxymethoxy)phenyl]acetic acid methyl ester (60 mg, 0.14 mmol) obtained above, using methanol (4 mL) and concentrated hydrochloric acid (0.10 mL).

$^1$H-NMR (270 MHz, CDCl$_3$) δ(ppm): 1.02 (t, J=7.4 Hz, 3H), 2.20-2.80 (m, 2H), 2.91 (brs, 3H), 3.35-3.60 (m, 2H), 3.77 (s, 3H), 4.00-5.00 (m, 2H), 5.89 (s, 1H), 6.98 (brs, 1H), 7.20-7.40 (m, 5H), 7.72 (brs, 1H); APCI-MS (m/z): 358 (M+H)$^+$.

Example 14

[2-Ethyl-3,5-dihydroxy-6-(morpholinocarbonyl)phenyl]acetic acid methyl ester (Compound 14)

(Step 1)

In a similar manner to Step 1 of Example 1, [2-ethyl-3,5-bis(methoxymethoxy)-6-(morpholinocarbonyl)phenyl]acetic acid methyl ester (82 mg, 86%) was obtained from 3-ethyl-2-(methoxycarbonylmethyl)-4,6-bis(methoxymethoxy)benzoic acid (79 mg, 0.23 mmol) obtained in Step 3 of Example 11, using tetrahydrofuran (4 mL), dichloromethane (1 mL), morpholine (0.061 mL, 0.70 mmol), 1-hydroxybenzotriazole monohydrate (0.15 g, 0.98 mmol) and 1-[3-(dimethylamino)propyl]-3-ethylcarbodiimide hydrochloride (0.27 g, 1.4 mmol).

$^1$H-NMR (270 MHz, CDCl$_3$) δ(ppm): 1.06 (t, J=7.5 Hz, 3H), 2.40-2.75 (m, 2H), 3.20-3.90 (m, 10H), 3.46 (s, 3H), 3.48 (s, 3H), 3.69 (s, 3H), 5.13 (s, 2H), 5.19 (s, 2H), 6.88 (s, 1H).

(Step 2)

In a similar manner to Step 2 of Example 1, Compound 14 (50 mg, 80%) was obtained from [2-ethyl-3,5-bis(methoxymethoxy)-6-(morpholinocarbonyl)phenyl]acetic acid methyl ester (80 mg, 0.19 mmol) obtained above, using methanol (4 mL) and concentrated hydrochloric acid (0.10 mL).

$^1$H-NMR (270 MHz, CDCl$_3$) δ(ppm): 1.04 (t, J=7.4 Hz, 3H), 2.53 (q, J=7.4 Hz, 2H), 3.45-3.80 (m, 13H), 6.18 (s, 1H); APCI-MS (m/z): 322 (M–H)$^-$.

Example 15

[2-Ethyl-3,5-dihydroxy-6-(N-methyl-N-propylcarbamoyl)phenyl]acetic acid methyl ester (Compound 15)

(Step 1)

In a similar manner to Step 1 of Example 1, [2-ethyl-3,5-bis(methoxymethoxy)-6-(N-methyl-N-propylcarbamoyl)phenyl]acetic acid methyl ester (61 mg, 55%) was obtained from 3-ethyl-2-(methoxycarbonylmethyl)-4,6-bis(methoxymethoxy)benzoic acid (96 mg, 0.28 mmol) obtained in Step 3 of Example 11, using tetrahydrofuran (4 mL), dichloromethane (1 mL), N-methylpropylamine (0.070 mL, 0.68 mmol), 1-hydroxybenzotriazole monohydrate (0.15 g, 0.98 mmol) and 1-[3-(dimethylamino)propyl]-3-ethylcarbodiimide hydrochloride (0.21 g, 1.1 mmol).

$^1$H-NMR (300 MHz, CDCl$_3$) δ(ppm): 0.97 (t, J=7.4 Hz, 3H), 1.06 (t, J=7.5 Hz, 3H), 1.65 (tq, J=7.4, 7.4 Hz, 2H), 2.45-2.75 (m, 2H), 3.06 (s, 3H), 3.40-3.60 (m, 2H), 3.46 (s, 3H), 3.48 (s, 3H), 3.64 (d, J=17.1 Hz, 1H), 3.66 (s, 3H), 3.83 (d, J=17.1 Hz, 1H), 5.11 (d, J=8.3 Hz, 1H), 5.14 (d, J=8.3 Hz, 1H), 5.19 (s, 2H), 6.86 (s, 1H).

(Step 2)

In a similar manner to Step 2 of Example 1, Compound 15 (42 mg, 91%) was obtained from [2-ethyl-3,5-bis(methoxymethoxy)-6-(N-methyl-N-propylcarbamoyl)phenyl]acetic acid methyl ester (60 mg, 0.15 mmol) obtained above, using methanol (4 mL) and concentrated hydrochloric acid (0.10 mL).

$^1$H-NMR (270 MHz, CDCl$_3$) δ(ppm): 0.89 (t, J=7.3 Hz, 3H), 1.61 (t, J=7.4 Hz, 3H), 1.61 (tq, J=7.3, 7.3 Hz, 2H), 2.52 (q, J=7.4 Hz, 2H), 2.93 (brs, 3H), 3.20-3.70 (m, 7H), 6.08-6.18 (m, 1H); APCI-MS (m/z): 310 (M+H)$^+$.

Example 16

{2-Ethyl-3,5-dihydroxy-6-[N-(2-methoxyethyl)-N-methylcarbamoyl]phenyl}acetic acid methyl ester (Compound 16)

(Step 1)

In a similar manner to Step 1 of Example 1, {2-ethyl-6-[N-(2-methoxyethyl)-N-methylcarbamoyl]-3,5-bis(methoxymethoxy)phenyl}acetic acid methyl ester (0.10 g, 87%) was obtained from 3-ethyl-2-(methoxycarbonylmethyl)-4,6-bis(methoxymethoxy)benzoic acid (96 mg, 0.28 mmol) obtained in Step 3 of Example 11, using tetrahydrofuran (4 mL), dichloromethane (1 mL), 2-methoxy-N-methylethylamine (0.070 mL, 0.65 mmol), 1-hydroxybenzotriazole monohydrate (0.15 g, 0.98 mmol) and 1-[3-(dimethylamino)propyl]-3-ethylcarbodiimide hydrochloride (0.25 g, 1.3 mmol).

$^1$H-NMR (300 MHz, CDCl$_3$) δ(ppm): 1.06 (t, J=7.4 Hz, 3H), 2.35-2.75 (m, 2H), 2.91 (s, 3H), 3.30-4.00 (m, 6H), 3.37 (s, 3H), 3.46 (s, 3H), 3.48 (s, 3H), 3.67 (s, 3H), 5.12 (d, J=12.5 Hz, 1H), 5.14 (d, J=12.5 Hz, 1H), 5.19 (s, 2H), 6.86 (s, 1H).

(Step 2)

In a similar manner to Step 2 of Example 1, Compound 16 (65 mg, 84%) was obtained from {2-ethyl-6-[N-(2-methoxyethyl)-N-methylcarbamoyl]-3,5-bis(methoxymethoxy)phenyl}acetic acid methyl ester (98 mg, 0.24 mmol) obtained above, using methanol (4 mL) and concentrated hydrochloric acid (0.10 mL).

$^1$H-NMR (270 MHz, CDCl$_3$) δ(ppm): 1.04 (t, J=7.5 Hz, 3H), 2.35-2.70 (m, 2H), 3.01 (brs, 3H), 3.36 (brs, 3H), 3.40-3.80 (m, 6H), 3.74 (s, 3H), 5.96 (s, 1H), 6.69 (brs, 1H), 7.53 (brs, 1H); APCI-MS (m/z): 326 (M+H)$^+$.

Example 17

[2-Ethyl-3,5-dihydroxy-6-(piperidinocarbonyl)phenyl]acetic acid methyl ester (Compound 17)

(Step 1)

In a similar manner to Step 1 of Example 1, [2-ethyl-3,5-bis(methoxymethoxy)-6-(piperidinocarbonyl)phenyl]acetic acid methyl ester (57 mg, 49%) was obtained from 3-ethyl-2-(methoxycarbonylmethyl)-4,6-bis(methoxymethoxy)benzoic acid (96 mg, 0.28 mmol) obtained in Step 3 of Example 11, using tetrahydrofuran (4 mL), dichloromethane (1 mL), piperidine (0.070 mL, 0.71 mmol), 1-hydroxybenzotriazole monohydrate (0.16 g, 1.0 mmol) and 1-[3-(dimethylamino)propyl]-3-ethylcarbodiimide hydrochloride (0.27 g, 1.4 mmol).

$^1$H-NMR (300 MHz, CDCl$_3$) δ(ppm): 1.06 (t, J=7.4 Hz, 3H), 1.40-1.70 (m, 6H), 2.40-2.75 (m, 2H), 3.10-3.50 (m, 4H), 3.46 (s, 3H), 3.48 (s, 3H), 3.65 (d, J=17.1 Hz, 1H), 3.68 (s, 3H), 3.78 (d, J=17.1 Hz, 1H), 5.12 (s, 2H), 5.19 (s, 2H), 6.88 (s, 1H).

(Step 2)

In a similar manner to Step 2 of Example 1, Compound 17 (41 mg, 95%) was obtained from [2-ethyl-3,5-bis(methoxymethoxy)-6-(piperidinocarbonyl)phenyl]acetic acid methyl ester (55 mg, 0.13 mmol) obtained above, using methanol (4 mL) and concentrated hydrochloric acid (0.10 mL).

$^1$H-NMR (270 MHz, CDCl$_3$) δ(ppm): 1.04 (t, J=7.4 Hz, 3H), 1.45-1.70 (m, 6H), 2.49 (brq, J=7.4 Hz, 2H), 3.53 (s, 2H), 3.35-3.65 (m, 4H), 3.75 (s, 3H), 5.90 (s, 1H), 6.85 (brs, 1H), 7.59 (brs, 1H); APCI-MS (m/z): 322 (M+H)$^+$.

Example 18

[2-Ethyl-3,5-dihydroxy-6-(4-methylpiperazin-1-ylcarbonyl)phenyl]acetic acid methyl ester (Compound 18)

(Step 1)

In a similar manner to Step 1 of Example 1, [2-ethyl-3,5-bis(methoxymethoxy)-6-(4-methylpiperazin-1-ylcarbonyl)phenyl]acetic acid methyl ester (94 mg, 79%) was obtained from 3-ethyl-2-(methoxycarbonylmethyl)-4,6-bis(methoxymethoxy)benzoic acid (96 mg, 0.28 mmol) obtained in Step 3 of Example 11, using tetrahydrofuran (4 mL), dichloromethane (1 mL), N-methylpiperazine (0.070 mL, 0.63 mmol), 1-hydroxybenzotriazole monohydrate (0.17 g, 1.1 mmol) and 1-[3-(dimethylamino)propyl]-3-ethylcarbodiimide hydrochloride (0.26 g, 1.4 mmol).

$^1$H-NMR (300 MHz, CDCl$_3$) δ(ppm): 1.06 (t, J=7.4 Hz, 3H), 2.30 (s, 3H), 2.15-2.75 (m, 6H), 3.26-3.94 (m, 4H), 3.45 (s, 3H), 3.48 (s, 3H), 3.65 (d, J=17.1 Hz, 1H), 3.68 (s, 3H), 3.79 (d, J=17.1 Hz, 1H), 5.12 (s, 2H), 5.19 (s, 2H), 6.88 (s, 1H).

(Step 2)

In a similar manner to Step 2 of Example 1, Compound 18 (36 mg, 49%) was obtained from [2-ethyl-3,5-bis(methoxymethoxy)-6-(4-piperazin-1-ylcarbonyl)phenyl]acetic acid methyl ester (55 mg, 0.13 mmol) obtained above, using methanol (4 mL) and concentrated hydrochloric acid (0.10 mL).

$^1$H-NMR (270 MHz, CDCl$_3$) δ(ppm): 1.04 (t, J=7.4 Hz, 3H), 2.45-2.65 (m, 2H), 2.82 (s, 3H), 3.00-4.00 (m, 10H), 3.68 (s, 3H), 6.26 (s, 1H); APCI-MS (m/z): 337 (M+H)$^+$.

Example 19

N-benzyl-3-ethyl-4,6-dihydroxy-2-(2-hydroxyethyl)benzamide (Compound 19)

(Step 1)

In a similar manner to Step 1 of Example 1, [2-(N-benzylcarbamoyl)-6-ethyl-3,5-bis(methoxymethoxy)phenyl]acetic acid methyl ester (0.11 g, 84%) was obtained from 3-ethyl-2-(methoxycarbonylmethyl)-4,6-bis(methoxymethoxy)benzoic acid (0.13 g, 0.29 mmol) obtained in Step 3 of Example 11, using tetrahydrofuran (4 mL), dichloromethane (1 mL), benzylamine (0.10 mL, 0.92 mmol), 1-hydroxybenzotriazole monohydrate (0.25 g, 1.6 mmol) and 1-[3-(dimethylamino)propyl]-3-ethylcarbodiimide hydrochloride (0.27 g, 1.4 mmol).

$^1$H-NMR (300 MHz, CDCl$_3$) δ(ppm): 1.03 (t, J=7.4 Hz, 3H), 2.55 (q, J=7.4 Hz, 2H), 3.43 (s, 3H), 3.46 (s, 3H), 3.57 (s, 3H), 3.72 (s, 2H), 4.60 (d, J=5.9 Hz, 2H), 5.14 (s, 2H), 5.18 (s, 2H), 6.47 (brt, J=5.9 Hz, 1H), 6.87 (s, 1H), 7.20-7.40 (m, 5H).

(Step 2)

The above-obtained [2-(N-benzylcarbamoyl)-6-ethyl-3,5-bis(methoxymethoxy)phenyl]acetic acid methyl ester (46 mg, 0.11 mmol) was dissolved in tetrahydrofuran (5 mL) and cooled to 0° C. The obtained solution was added with 1.0 mol/L lithium aluminum hydride-tetrahydrofuran solution (0.20 mL, 0.20 mmol) followed by stirring at 0° C. for 0.5 hour. The reaction mixture was added with saturated aqueous sodium sulfate solution, and was extracted with ethyl acetate 3 times. The organic layers were combined, washed with saturated brine, dried over anhydrous sodium sulfate and then the solvent was evaporated under reduced pressure. The residue was purified by preparative thin-layer chromatography (hexane/ethyl acetate=1/1) to obtain N-benzyl-3-ethyl-2-(2-hydroxyethyl)-4,6-bis(methoxymethoxy)benzamide (30 mg, 74%).

$^1$H-NMR (300 MHz, CDCl$_3$) δ(ppm): 1.10 (t, J=7.4 Hz, 3H), 2.65 (q, J=7.4 Hz, 2H), 2.92 (t, J=6.1 Hz, 2H), 3.37 (s, 3H), 3.47 (s, 3H), 3.86 (dt, J=4.6, 6.1 Hz, 2H), 4.30 (brt, J=4.6 Hz, 1H), 4.66 (d, J=5.8 Hz, 2H), 5.09 (s, 2H), 5.19 (s, 2H), 6.31 (brt, J=5.8 Hz, 1H), 6.81 (s, 1H), 7.22-7.46 (m, 5H).

(Step 3)

In a similar manner to Step 2 of Example 1, Compound 19 (12 mg, 46%) was obtained from N-benzyl-3-ethyl-2-(2-hydroxyethyl)-4,6-bis(methoxymethoxy)benzamide (31 mg, 0.79 mmol) obtained above, using ethanol (4 mL) and concentrated hydrochloric acid (0.10 mL).

$^1$H-NMR (270 MHz, CDCl$_3$) δ(ppm): 1.09 (t, J=7.4 Hz, 3H), 2.39 (brs, 1H), 2.55 (q, J=7.4 Hz, 2H), 3.04 (t, J=5.5 Hz, 2H), 4.02 (brt, J=5.5 Hz, 2H), 4.61 (d, J=5.5 Hz, 2H), 5.36

(brs, 1H), 6.26 (s, 1H), 7.20-7.40 (m, 5H), 8.91 (brs, 1H), 10.12 (brs, 1H); APCI-MS (m/z): 314 (M−H)⁻.

Example 20

3-Ethyl-4,6-dihydroxy-2-[2-(2-methoxyethoxy) ethyl]phenyl=morpholino=ketone (Compound 20)

(Step 1)
[2-Ethyl-3,5-bis(methoxymethoxy)-6-(morpholinocarbonyl)phenyl]acetic acid methyl ester (0.59 g, 1.4 mmol) obtained in Step 1 of Example 14 was dissolved in tetrahydrofuran (8 mL), and cooled to 0° C. The obtained solution was added with lithium aluminum hydride (77 mg, 2.0 mmol) followed by stirring at 0° C. for 0.5 hour. The reaction mixture was added with anhydrous sodium sulfate and saturated aqueous sodium sulfate solution, stirred at a room temperature for 2 hours and then filtered. The obtained filtrate was concentrated under reduced pressure to obtain 3-ethyl-2-(2-hydroxyethyl)-4,6-bis(methoxymethoxy) phenyl=morpholino=ketone (0.47 g, 85%).
$^1$H-NMR (300 MHz, CDCl$_3$) δ(ppm): 1.12 (t, J=7.4 Hz, 3H), 2.50-3.60 (m, 15H), 3.46 (s, 3H), 3.50 (s, 3H), 5.13 (s, 2H), 5.19 (d, J=9.9 Hz, 1H), 5.21 (d, J=9.9 Hz, 1H), 6.83 (s, 1H).

(Step 2)
The above-obtained 3-ethyl-2-(2-hydroxyethyl)-4,6-bis(methoxymethoxy)phenyl=morpholino=ketone (0.15 g, 0.39 mmol) was dissolved in N,N-dimethylformamide (5 mL) and the obtained solution was added with 60% sodium hydride-oil dispersion (0.10 g, 2.5 mmol), followed by stirring at a room temperature for 1 hour. The mixture was added with 2-bromoethyl methyl ether (0.10 mL, 1.1 mmol) and stirred at 60° C. for 12 hours. Then, the reaction mixture was added with water and extracted with chloroform 3 times. The organic layers were combined, washed with saturated brine, dried over anhydrous sodium sulfate and then evaporated under reduced pressure. The residue was purified by preparative thin-layer chromatography (chloroform/methanol=20/1) to obtain 3-ethyl-2-[2-(2-methoxyethoxy)ethyl]-4,6-bis (methoxymethoxy)phenyl=morpholino=ketone (94 mg, 55%).
$^1$H-NMR (300 MHz, CDCl$_3$) δ(ppm): 1.11 (t, J=7.4 Hz, 3H), 2.50-4.00 (m, 18H), 5.05-5.20 (m, 4H), 6.80 (s, 1H).

(Step 3)
In a similar manner to Step 2 of Example 1, Compound 20 (69 mg, 93%) was obtained from 3-ethyl-2-[2-(2-methoxyethoxy)ethyl]-4,6-bis(methoxymethoxy) phenyl=morpholino=ketone (93 mg, 0.21 mmol) obtained above, using ethanol (4 mL) and concentrated hydrochloric acid (0.10 mL).
$^1$H-NMR (300 MHz, CDCl$_3$) δ(ppm): 1.03 (t, J=7.3 Hz, 3H), 2.50-3.00 (m, 2H), 3.20-4.00 (m, 14H), 3.38 (s, 3H), 6.00 (s, 1H), 7.48 (brs, 1H), 8.01 (brs, 1H); APCI-MS (m/z): 354 (M+H)⁺.

Example 21

3-Ethyl-4,6-dihydroxy-2-(2-hydroxyethyl) phenyl=morpholino=ketone (Compound 21)

3-Ethyl-2-(2-hydroxyethyl)-4,6-bis(methoxymethoxy) phenyl=morpholino=ketone (0.10 g, 0.26 mmol) obtained in Step 1 of Example 20 was dissolved in ethanol (4 mL), and the obtained solution was added with concentrated hydrochloric acid (0.10 mL) followed by stirring at 60° C. for 1 hour. The reaction mixture was concentrated under reduced pressure and the residue was purified by preparative thin-layer chromatography (chloroform/methanol=9/1) to obtain Compound 21 (21 mg, 28%).
$^1$H-NMR (270 MHz, CDCl$_3$-CD$_3$OD) δ(ppm): 1.11 (t, J=7.4 Hz, 3H), 2.50-4.00 (m, 14H), 6.16 (s, 1H); APCI-MS (m/z): 296 (M+H)⁺.

Example 22

2-(Benzyloxymethyl)-4,6-dihydroxybenzoic acid methyl ester (Compound 22)

(Step 1)
3,5-Dihydroxybenzoic acid methyl ester (11 g, 63 mmol) was dissolved in dichloromethane (0.10 L), and obtained solution was added with N,N-diisopropylethylamine (32 mL, 190 mmol) and chloromethyl methyl ether (14 mL, 190 mmol) followed by stirring at a room temperature for 5 hours. The reaction mixture was added with water and extracted with ethyl acetate 3 times. The organic layers were combined, washed with saturated brine, dried over anhydrous sodium sulfate and then the solvent was evaporated under reduced pressure. The obtained residue was purified by silica gel column chromatography (chloroform) to obtain 3,5-bis (methoxymethoxy)benzoic acid methyl ester (14 g, 87%).
$^1$H-NMR (270 MHz, CDCl$_3$) δ(ppm): 3.48 (s, 6H), 3.90 (s, 3H), 5.19 (s, 4H), 6.85-6.95 (m, 1H), 7.30-7.40 (m, 2H).

(Step 2)
The above-obtained 3,5-bis(methoxymethoxy)benzoic acid methyl ester (9.1 g, 36 mmol) was dissolved in diethylether (50 mL) and cooled to 0° C. To the obtained solution, lithium aluminum hydride (2.0 g, 54 mmol) was slowly added followed by stirring at 0° C. for 2 hours. The reaction mixture was further added with sodium sulfate decahydrate (40 g), and was stirred for another 1 hour. The reaction mixture was filtered, and the obtained filtrate was concentrated under reduced pressure to obtain 3,5-bis(methoxymethoxy)phenylmethanol (7.6 g, 94%).
$^1$H-NMR (270 MHz, CDCl$_3$) δ(ppm): 2.01 (brs, 1H), 3.47 (s, 6H), 4.62 (d, J=6.0 Hz, 2H), 5.15 (s, 4H), 6.60-6.75 (m, 3H).

(Step 3)
The above-obtained 3,5-bis(methoxymethoxy)phenylmethanol (5.3 g, 23 mmol) was dissolved in N,N-dimethylformamide (20 mL) and obtained solution was added with N-bromosuccinimide (4.3 g, 24 mmol) followed by stirring at a room temperature for 5 hours. The reaction mixture was added with water and extracted with chloroform 3 times. The organic layers were combined, washed with saturated brine, dried over anhydrous sodium sulfate and then the solvent was evaporated under reduced pressure. The residue was purified by silica gel column chromatography (hexane/ethyl acetate=9/1 to 5/1 to 2/1) to obtain [2-bromo-3,5-bis(methoxymethoxy)phenyl]methanol (4.9 g, 69%).
$^1$H-NMR (270 MHz, CDCl$_3$) δ(ppm): 2.18 (brt, J=6.5 Hz, 1H), 3.47 (s, 3H), 3.52 (s, 3H), 4.72 (d, J=6.5 Hz, 2H), 5.17 (s, 2H), 5.23 (s, 2H), 6.81 (d, J=2.6 Hz, 1H), 6.91 (d, J=2.6 Hz, 1H).

(Step 4)
The above-obtained [2-bromo-3,5-bis(methoxymethoxy) phenyl]methanol (3.5 g, 11 mmol) was dissolved in N,N-dimethylformamide (20 mL) and cooled to 0° C. The obtained solution was added with 60% sodium hydride-oil dispersion (0.59 g, 15 mmol) and benzyl bromide (2.0 mL, 17 mmol), followed by stirring at a room temperature for 1 hour. The reaction mixture was added with methanol and water and extracted with chloroform 3 times. The organic layers were combined, washed with saturated brine, dried over anhydrous sodium sulfate and then the solvent was evaporated under reduced pressure. The residue was purified by silica gel column chromatography (hexane/ethyl acetate=20/1 to 10/1) to obtain 2-bromo-1-(benzyloxymethyl)-3,5-bis(methoxymethoxy)benzene (3.2 g, 70%).

$^1$H-NMR (270 MHz, CDCl$_3$) δ(ppm): 3.47 (s, 3H), 3.52 (s, 3H), 4.61 (s, 2H), 4.64 (s, 2H), 5.16 (s, 2H), 5.23 (s, 2H), 6.81 (d, J=2.7 Hz, 1H), 6.97 (d, J=2.7 Hz, 1H), 7.20-7.42 (m, 5H).

(Step 5)

The above-obtained 2-bromo-1-(benzyloxymethyl)-3,5-bis(methoxymethoxy)benzene (1.6 g, 4.3 mmol) was dissolved in diethylether (25 mL) and cooled to −78° C. The obtained solution was added with 1.52 mol/L n-butyllithium-hexane solution (4.0 mL, 6.1 mmol) and stirred at −78° C. for 1 hour. Then, N,N-dimethylformamide (1.0 mL, 13 mmol) was added thereto and stirred at a room temperature for 3 hours. The reaction mixture was added with water and methanol, and then extracted with chloroform 3 times. The organic layers were combined, washed with saturated brine, and then dried over anhydrous sodium sulfate. Then the solvent was evaporated under reduced pressure. The residue was purified by silica gel column chromatography (hexane/ethyl acetate=10/1 to 5/1 to 3/1) to obtain 2-(benzyloxymethyl)-4,6-bis(methoxymethoxy)benzaldehyde (0.99 g, 72%).

$^1$H-NMR (270 MHz, CDCl$_3$) δ(ppm): 3.49 (s, 3H), 3.51 (s, 3H), 4.67 (s, 2H), 4.97 (s, 2H), 5.24 (s, 2H), 5.27 (s, 2H), 6.76 (d, J=2.3 Hz, 1H), 7.17 (d, J=2.3 Hz, 1H), 7.22-7.46 (m, 5H), 10.48 (s, 1H).

(Step 6)

The above-obtained 2-(benzyloxymethyl)-4,6-bis(methoxymethoxy)benzaldehyde (0.80 g, 2.3 mmol) was dissolved in tert-butyl alcohol (20 mL) and the obtained solution was added with 2-methyl-2-butene (10 mL, 94 mmol), sodium chlorite (2.0 g, 22 mmol), sodium dihydrogen phosphate (2.0 g, 17 mmol) and water (5 mL), followed by stirring at a room temperature for 10 hours. The reaction mixture was extracted with chloroform 3 times. The organic layers were combined, washed with saturated brine, dried over anhydrous sodium sulfate. Then the solvent was evaporated under reduced pressure to obtain 2-(benzyloxymethyl)-4,6-bis(methoxymethoxy)benzoic acid (0.94 g, 100%).

$^1$H-NMR (270 MHz, CDCl$_3$) δ(ppm): 3.48 (s, 3H), 3.52 (s, 3H), 4.61 (s, 2H), 4.84 (s, 2H), 5.20 (s, 2H), 5.29 (s, 2H), 6.83 (d, J=2.3 Hz, 1H), 7.09 (d, J=2.3 Hz, 1H), 7.24-7.42 (m, 5H).

(Step 7)

The above-obtained 2-(benzyloxymethyl)-4,6-bis(methoxymethoxy)benzoic acid (20 mg, 0.054 mmol) was dissolved in methanol (2 mL) and the obtained solution was added with 2.0 mol/L trimethylsilyldiazomethane-hexane solution (0.30 mL, 0.60 mmol), followed by stirring at a room temperature for 1 hour. The reaction mixture was added with acetic acid (0.050 mL) and the solvent was evaporated under reduced pressure. The residue was purified by preparative thin-layer chromatography (chloroform/methanol=100/1) to obtain 2-(benzyloxymethyl)-4,6-bis(methoxymethoxy)benzoic acid methyl ester (12 mg, 57%).

$^1$H-NMR (270 MHz, CDCl$_3$) δ(ppm): 3.47 (s, 3H), 3.47 (s, 3H), 3.79 (s, 3H), 4.50 (s, 2H), 4.56 (s, 2H), 5.17 (s, 4H), 6.78 (s, 2H), 7.20-7.40 (m, 5H).

(Step 8)

The above-obtained 2-(benzyloxymethyl)-4,6-bis(methoxymethoxy)benzoic acid methyl ester (10 mg, 0.027 mmol) was dissolved in ethanol (4 mL) and the obtained solution was added with concentrated hydrochloric acid (0.10 mL) and stirred at 60° C. for 1 hour. The reaction mixture was concentrated under reduced pressure, and the residue was purified by preparative thin-layer chromatography (chloroform/methanol=20/1) to obtain Compound 22 (12 mg, 100%).

$^1$H-NMR (270 MHz, CDCl$_3$) δ(ppm): 3.89 (s, 3H), 4.64 (s, 2H), 4.80 (brs, 1H), 5.49 (brs, 1H), 6.35 (d, J=2.6 Hz, 1H), 6.77 (dt, J=2.6, 1.0 Hz, 1H), 7.20-7.50 (m, 5H), 11.58 (brs, 1H); APCI-MS (m/z): 287 (M−H)$^-$.

REFERENCE EXAMPLE 1

3-Ethyl-4,6-dihydroxy-2-(methoxycarbonylmethyl)benzoic acid methyl ester (Compound 23)

(Step 1)

3-Oxohexanoic acid ethyl ester (20 mL, 0.13 mol) was dissolved in toluene (100 mL), and the obtained solution was added with triethylamine (28 mL, 0.20 mol) and chlorotrimethylsilane (24 mL, 0.19 mmol), followed by stirring at a room temperature for 4 hours. The reaction mixture was added with hexane (200 mL) and 0.5 mol/L aqueous sodium hydrogencarbonate solution and then, extracted with hexane 3 times. The organic layers were combined, sequentially washed with saturated aqueous sodium hydrogencarbonate solution and saturated brine, dried over anhydrous sodium sulfate, and then evaporated under reduced pressure. The residue was dissolved in tetrahydrofuran (100 mL) and cooled to −78° C. The obtained solution was added with 2.0 mol/L lithiumdiisopropylamide-tetrahydrofuran solution (78 mL, 0.16 mol) followed by stirring at −78° C. for 1 hour. Then, chlorotrimethylsilane (18 mL, 0.14 mol) was added and the reaction mixture was stirred at −78° C. for 8 hours. The reaction mixture was further added with hexane (200 mL) and water and extracted with hexane 3 times. The organic layers were combined, sequentially washed with saturated aqueous sodium hydrogencarbonate solution and saturated brine, dried over anhydrous sodium sulfate, and then evaporated under reduced pressure to obtain 1-ethoxy-1,3-bis(trimethylsiloxy)hexa-1,3-diene (41 g, 100%).

$^1$H-NMR (270 MHz, CDCl$_3$) δ(ppm): 0.17 (s, 9H), 0.24 (s, 9H), 0.94 (t, J=7.1 Hz, 3H), 1.29 (t, J=6.5 Hz, 3H), 2.07 (dq, J=6.8, 7.1 Hz, 2H), 3.73 (q, J=6.5 Hz, 2H), 3.86 (s, 1H), 4.85 (t, J=6.8 Hz, 1H).

(Step 2)

3-Oxopentanedioic acid dimethyl ester (11 mL, 75 mmol) was dissolved in dichloromethane (100 mL), and cooled to 0° C. The obtained solution was added with 2-chloro-1,3-dimethylimidazolium chloride (14 g, 83 mmol) and triethylamine (31 mL, 0.23 mol), warmed up to a room temperature and stirred for 4 hours. The reaction mixture was added with hexane (200 mL) and water and extracted with hexane 3 times. The organic layers were combined and sequentially washed with water and saturated brine, dried over anhydrous sodium sulfate and then evaporated under reduced pressure. The residue was purified by silica gel column chromatography (hexane/ethyl acetate=2/1) to obtain penta-2,3-dienedioic acid dimethyl ester (4.7 g, 40%).

$^1$H-NMR (270 MHz, CDCl$_3$) δ (ppm): 3.78 (s, 6H), 6.05 (s, 2H).

(Step 3)

The above-obtained penta-2,3-dienedioic acid dimethyl ester (4.6 g, 30 mmol) and 1-ethoxy-1,3-bis(trimethylsiloxy) hexa-1,3-diene (13 g, 41 mmol) were mixed and stirred at a room temperature for 1.5 hours. The reaction mixture was added with ethanol (100 mL) and ammonium fluoride (5.4 g) and stirred at a room temperature for 2 hours. The reaction mixture was further added with water and extracted with ethyl acetate 3 times. The organic layers were combined, sequentially washed with water and saturated brine, dried over anhydrous sodium sulfate and then the solvent was evaporated under reduced pressure. The residue was triturated with hexane (50 mL) to obtain Compound 23 (3.2 g, 40%).

$^1$H-NMR (270 MHz, CDCl$_3$) δ(ppm): 1.06 (t, J=7.5 Hz, 3H), 2.61 (q, J=7.5 Hz, 2H), 3.71 (s, 3H), 3.85 (s, 3H), 3.95 (s, 2H), 6.35 (s, 1H); APCI-MS (m/z): 269 (M+H)$^+$.

INDUSTRIAL APPLICABILITY

The present invention provides Hsp90 family protein inhibitors comprising, as an active ingredient, a benzoic acid derivative or a prodrug thereof, or a pharmaceutically acceptable salt of said benzoic acid derivative or said prodrug, and the like.

The invention claimed is:

1. A method for inhibiting heat shock protein 90 family protein comprising administering, to a patient in need thereof, an effective amount of a compound represented by Formula (I):

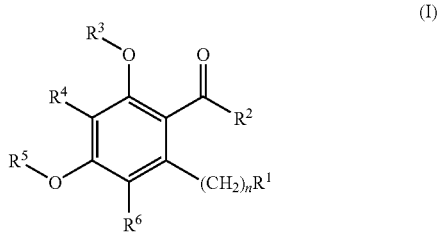

(wherein n represents an integer of 0 to 2;

R$^1$ represents a hydrogen atom, hydroxy, substituted or unsubstituted lower alkoxycarbonyl, or —OR$^{13}$ (wherein R$^{13}$ represents substituted or unsubstituted lower alkyl, or substituted or unsubstituted aralkyl;

R$^2$ represents —NR$^{14}$R$^{15}$ (wherein R$^{14}$ and R$^{15}$ may be the same or different and each represents a hydrogen atom, substituted or unsubstituted lower alkyl, substituted or unsubstituted aryl, substituted or unsubstituted aralkyl, or substituted or unsubstituted heterocyclic alkyl, or R$^{14}$ and R$^{15}$ are combined together with the adjacent nitrogen atom thereto to form a substituted or unsubstituted heterocyclic group) or —OR$^{16}$ (wherein R$^{16}$ represents substituted or unsubstituted lower alkyl);

R$^3$, R$^4$ and R$^5$ each represents a hydrogen atom; and

R$^6$ represents a hydrogen atom, halogen, or substituted or unsubstituted lower alkyl, or a pharmaceutically acceptable salt thereof.

2. The method according to claim 1, wherein R$^1$ is substituted or unsubstituted lower alkoxycarbonyl.

3. The method according to claim 1, wherein R$^1$ is —OR$^{13}$.

4. The method according to any one of claims 1, 2 and 3, wherein R$^2$ is —NR$^{14b}$R$^{15b}$ (wherein R$^{14b}$ and R$^{15b}$ independently represent a hydrogen atom, substituted or unsubstituted lower alkyl, substituted or unsubstituted aryl, substituted or unsubstituted aralkyl, or substituted or unsubstituted heterocyclic alkyl).

5. The method according to any one of claims 1, 2 and 3, wherein R$^2$ is —NR$^{14c}$R$^{15c}$ (wherein R$^{14c}$ and R$^{15c}$ are combined together with the adjacent nitrogen atom thereto to form a substituted or unsubstituted heterocyclic group).

6. A method for treating mammary cancer, comprising administering, to a patient in need thereof, an effective amount of the compound, or said pharmaceutically acceptable salt thereof described in claim 1.

7. A method for treating leukemia, comprising administering, to a patient in need thereof, an effective amount of the compound, or said pharmaceutically acceptable salt thereof described in claim 1.

8. A method for treating chronic myelocytic leukemia, comprising administering, to a patient in need thereof, an effective amount of the compound, or said pharmaceutically acceptable salt thereof described in claim 1.

* * * * *

UNITED STATES PATENT AND TRADEMARK OFFICE
CERTIFICATE OF CORRECTION

PATENT NO. : 7,781,485 B2
APPLICATION NO. : 11/718079
DATED : August 24, 2010
INVENTOR(S) : Yushi Kitamura et al.

It is certified that error appears in the above-identified patent and that said Letters Patent is hereby corrected as shown below:

ON TITLE PAGE COL. 2 AT (56) OTHER PUBLICATIONS

Under "Wolff, M.E.,": ""Burqer's" should read --"Burger's--; and
Under "Yamaguchi, et al.,": "Polyclicic" should read --Polycyclic--.

COLUMN 7

Line 52, "have" should read --has--.

COLUMN 10

Line 35, "aliphatiic" should read --aliphatic--.

COLUMN 13

Line 59, "method" should read --methods--.

COLUMN 24

Line 31, "eight/10-fold" should read --eight $\sqrt{10}$-fold--.

COLUMN 25

Line 21, "treated the" should read --treated with the--.

COLUMN 36

Line 27, "J=7.4, 7.4 Hz," should read --J=7.4 Hz,--.

Signed and Sealed this

Twenty-first Day of December, 2010

David J. Kappos
*Director of the United States Patent and Trademark Office*

COLUMN 44

Line 2, "aralkyl;" should read --aralkyl);--; and
    Line 15, "alkyl," should read --alkyl),--.